US007700717B2

(12) United States Patent
Bonasera et al.

(10) Patent No.: US 7,700,717 B2
(45) Date of Patent: Apr. 20, 2010

(54) PHOTO-ACTIVE BACKBONE CYCLIZED SOMATOSTATIN ANALOGS FOR PHOTODYNAMIC THERAPY AND IMAGING

(75) Inventors: Thomas A. Bonasera, Milan (IL); Nurit Livnah, Mazkeret Batya (IL); Yoseph Salitra, Rehovot (IL); Tamar Yechezkel, Ramat-Gan (IL)

(73) Assignee: DeveloGen Israel Ltd., Rehovot (IL)

( * ) Notice: Subject to any disclaimer, the term of this patent is extended or adjusted under 35 U.S.C. 154(b) by 605 days.

(21) Appl. No.: 10/950,378

(22) Filed: Sep. 24, 2004

(65) Prior Publication Data

US 2005/0090429 A1    Apr. 28, 2005

Related U.S. Application Data

(63) Continuation of application No. PCT/IL03/00239, filed on Mar. 19, 2003.

(30) Foreign Application Priority Data

Mar. 26, 2002  (IL)  ..................... 148921

(51) Int. Cl.
*A61K 38/16* (2006.01)
(52) U.S. Cl. .................. 530/311; 514/6; 514/9
(58) Field of Classification Search ......... None
See application file for complete search history.

(56) References Cited

U.S. PATENT DOCUMENTS

| | | | |
|---|---|---|---|
| 5,149,708 A | 9/1992 | Dolphin et al. | 514/410 |
| 5,211,938 A | 5/1993 | Kennedy et al. | 424/7.1 |
| 5,308,608 A | 5/1994 | Dolphin et al. | 424/9 |
| 5,650,292 A | 7/1997 | Scherz et al. | 435/68.1 |
| 5,716,595 A | 2/1998 | Goldenberg | 414/1.49 |
| 5,723,575 A | 3/1998 | Gilon et al. | 530/317 |
| 5,726,169 A | 3/1998 | Scherz et al. | 514/185 |
| 5,770,687 A | 6/1998 | Hornik et al. | 530/311 |
| 5,779,867 A | 7/1998 | Bell et al. | 604/265 |
| 5,811,392 A | 9/1998 | Gilon et al. | 514/11 |
| 5,824,772 A | 10/1998 | Vincent et al. | 530/311 |
| 5,874,529 A | 2/1999 | Gilon et al. | 530/317 |
| 5,883,293 A | 3/1999 | Gilon et al. | 562/455 |
| 5,955,585 A | 9/1999 | Scherz et al. | 530/408 |
| 6,051,554 A | 4/2000 | Hornik et al. | 514/11 |
| 6,054,449 A | 4/2000 | Robinson et al. | 514/9 |
| 6,147,195 A | 11/2000 | Scherz et al. | 530/391.1 |
| 6,217,848 B1 | 4/2001 | Achilefu et al. | 424/9.1 |
| 6,265,375 B1 | 7/2001 | Gilon et al. | 514/9 |
| 6,316,215 B1 | 11/2001 | Adair et al. | 435/29 |
| 6,333,319 B1 | 12/2001 | Scherz et al. | 514/185 |
| 6,355,613 B1 | 3/2002 | Hornik et al. | 514/9 |

FOREIGN PATENT DOCUMENTS

| | | |
|---|---|---|
| JP | 200342297 | 12/2000 |
| WO | WO 95/33765 | 12/1995 |
| WO | WO 97/09344 | 3/1997 |
| WO | WO 98/04583 | 2/1998 |
| WO | WO 99/65508 * | 12/1999 |
| WO | WO 00/41727 | 7/2000 |
| WO | WO 00/61194 | 10/2000 |
| WO | WO 01/15694 | 3/2001 |
| WO | WO 02/20610 * | 3/2002 |
| WO | WO 02/062819 | 8/2002 |
| WO | WO 02/064163 | 8/2002 |
| WO | WO 03/003806 | 1/2003 |

OTHER PUBLICATIONS

Lazar et al., Molecular and Cellular Biology, 1988, vol. 8, No. 3, pp. 1247-1252.*
Marco Del Governatore et al., "Experimental Photoimmunotherapy of Hepatic Metastases of Colorectal Cancer with a 17.1A Chlorin e6 Immunoconjugate[1]", Cancer Research, vol. 60, pp. 4200-4255. (2000).
Stefania De Luca et al., "Synthesis and Solution Characterization of a Porphyrin-CCK8 Conjugate", Journal of Peptide Science, J. Peptide Sci., vol. 7: pp. 386-394 (2001).
David G. Hilmey et al., "Water-Soluble, Core-Modified Porphyrins as Novel, Longer-Wavelength-Absorbing Sensitizers for Photodynamic Therapy. II. Effects of Core Heteroatoms and Meso-Substituents on Biological Activity", Journal of Med. Chem., vol. 7: pp. 449-461 (2002).
Kai Licha et al., "Synthesis, Characterization, and Biological Properties of Cyanine-Labeled Somatostatin Analogues as Receptor-Targeted Fluorescent Probes", Bioconjugate Chem, vol. 12, pp. 44-50, (2001).
Achilefu et al., "Novel receptor-targeted fluorescent contrast agents for in vivo tumor imaging", Investigative Radiology, vol. 35, No. 8, pp. 479-485 (2000).
Allport et al., "In vivo imaging of gene and cell therapies", Exp. Hematol. vol. 29, pp. 1237-1246 (2001).
Aparici et al., "Somatostatin receptor scintigraphy predicts impending cardiac allograft rejection before endomyocardial biopsy", Eur. J. Nuc. Med., vol. 27, No. 12, pp. 1754-1759 (2000).
Becker et al., "Receptor-targeted optical imaging of tumors with near-infrared fluorescent ligands", Nat. Biotechnol., vol. 19, pp. 327-331 (2001).

(Continued)

*Primary Examiner*—Christopher R. Tate
*Assistant Examiner*—Roy Teller
(74) *Attorney, Agent, or Firm*—Winston & Strawn LLP

(57) ABSTRACT

Novel photo-active labeled diagnostic and therapeutic peptides which are conformationally constrained backbone cyclized somatostatin analogs, having improved somatostatin receptor subtype affinity and selectivity are disclosed. The backbone cyclized peptide analogs disclosed possess unique and superior properties over other analogs, such as chemical and metabolic stability, selectivity, increased bioavailability and improved pharmacokinetics. Furthermore, the unique patterns of receptor subtype selectivity provide compounds having improved diagnostic and therapeutic utilities. Pharmaceutical compositions comprising the photo-active backbone cyclized somatostatin analogs, reagents for synthesizing same, and methods of using such compositions for diagnostic and therapeutic purposes including optical imaging and photodynamic therapy are also disclosed.

30 Claims, 4 Drawing Sheets

OTHER PUBLICATIONS

Gilon et al., "Backbone cyclization: A new method for conferring conformational constraint on peptides", Biopolymers, vol. 31, pp. 745-750 (1991).

Lamberts et al., "The role of somatostatin in the regulation of anterior pituitary hormone secretion and the use of its analogs in the treatment of human pituitary tumors", Endocrine Rev., vol. 9, No. 4, pp. 417-436 (1988).

Lamberts et al., Drug Therapy: Octreotide, N. Engl. J. Med. 246, vol. 334, No. 4, pp. 246-254 (1996).

Landau et al., "A novel somatostatin analogue prevents early renal complications in the nonobese diabetic mouse", Kidney International, vol. 60, pp. 505-512 (2001).

Licha et al., "Synthesis, characterization, and biological properties of cyanine-labeled somatostatin analogues as receptor-targeted fluorescent probes", Bioconjugate Chem., vol. 12, pp. 44-50 (2001).

Okarvi, "Recent developments in $^{99}TC^m$-labelled peptide-based radiopharmaceuticals: An overview", Nuc. Med. Comm., vol. 20, pp. 1093-1112 (1999).

Raynor et al., "Cloned somatostatin receptors: identification of subtype-selective peptides and demonstration of high affinity binding of linear peptides", Molecular Pharmacology, vol. 43, pp. 838-844 (1993).

Reisine et al., "Molecular biology of somatostatin receptors", Endocrine Rev., vol. 16, No. 4, pp. 427-442 (1995).

* cited by examiner

USPTO Patent

PHOTO-ACTIVE BACKBONE CYCLIZED SOMATOSTATIN ANALOGS FOR PHOTODYNAMIC THERAPY AND IMAGING

CROSS-REFERENCE TO RELATED APPLICATIONS

This application is a continuation of International application PCT/IL2003/000239 filed Mar. 19, 2003, the content of which is expressly incorporated herein by reference.

FIELD OF THE INVENTION

The present invention relates to photo-active somatostatin analogs which are conformationally constrained $N^\alpha$ backbone-cyclized peptides, to pharmaceutical compositions containing same, to reagents for synthesizing same, and to methods for using such compounds for optical imaging and for photodynamic therapy.

BACKGROUND OF THE INVENTION

Somatostatin (SST) is a cyclic tetradecapeptide found in both the central nervous system and peripheral tissues. It was originally isolated from mammalian hypothalamus and identified as an important inhibitor of growth hormone secretion from the anterior pituitary. Its multiple biological activities include inhibition of the secretion of glucagon and insulin from the pancreas, regulation of most gut hormones and regulation of the release of other neurotransmitters involved in motor activity and cognitive processes throughout the central nervous system (for review see Lamberts, *Endocrine Rev.*, 9: 427, 1988). Additionally, SST and its analogs are potentially useful antiproliferative agents for the treatment of various types of tumors. In its natural form, SST has limited use as a therapeutic agent since it exhibits two undesirable properties: poor bioavailability and short duration of action. For these reasons, great efforts have been made to find SST analogs with superior potency, biostability, duration of action and selectivity.

The diverse physiological effects of SST are induced by five selective and high affinity binding to receptors (designated SST-R1 through SST-R5), that are members of the seven transmembrane segment receptor superfamily (reviewed in Reisine T., Bell G I., *Endocrinology Rev.*, 16: 427-442, 1995).

Somatostatin in Cancer and Radiolabelled SST Analog

Because SST receptors are present in high density in many endocrine and non-endocrine tumors, diagnosis and treatment were attempted using radiolabelled SST analogs in cancer patients. Most tumors express multiple SST receptor-subtypes, although the SST-R2 subtype is most predominantly expressed. Radiolabelled receptor-specific compounds can detect primary sites, identify occult metastatic lesions, guide surgical intervention, stage tumors, predict efficacy of certain therapeutic agents or, when labelled with suitable radionuclides, be useful radiotherapeutic agents. The abundance of high affinity SST receptors in various tumors enables the use of radiolabelled SST analogs for in vivo identification, visualization and localization of these tumors (Lamberts et al. *N. Engl. J. Med.* 334:246 1996).

Scintigraphy using radiolabelled SST analog tracers helps to localize tumors and to evaluate the potential for chronic treatment of patients with inoperable SST receptor-positive tumors.

Recently, a number of $^{99m}$Tc-labeled bioactive peptides have proven to be useful diagnostic imaging agents. Okarvi S. M. (*Nuc. Med. Comm.*, 20:1093, 1999) reviews the recent developments in $^{99}$Tc-labeled peptide-based radiopharmaceuticals. Another application of radiolabelled SST analogs is radio-guided surgery. This technique has been successfully utilized in surgery of medullary thyroid cancer, carcinoids and islet cell tumors.

SST receptor radio-imaging has been recently used successfully (Aparici et al. *Eur. J. Nuc. Med.* 27:1754, 2000), for detection of cardiac allograft rejection. Infiltrated activated lymphocytes express SST receptors thus SST receptor imaging could be used to target them.

Optical Imaging

With the clinical success of radiopeptides as diagnostics and therapeutics, interest in the optical imaging of tumors using fluorescent-labeled peptides has been increasing. In addition, in vivo optical imaging is used to assess specific molecular targets for gene- and cell-based therapies (Allport et al. Exp. Hematol. 29, 1237-1246, 2001). In optical imaging (known also as photodynamic diagnosis or PDD), the patient is neither exposed to externally administered ionizing radiation (e.g., CT) nor injected with radioactive materials (e.g., nuclear medicine radiopharmaceuticals); thus, avoiding both radiation and radioactivity, the technique is more acceptable to the general public. The use of peptide conjugates for optical imaging, demonstrated by in vivo targeting to the somatostatin receptor in rats bearing receptor-expressing tumors have been reported by Licha et al. (Bioconjugate Chem. 12, 44-50, 2001) and Achilefu et al. (Investigative Radiology 35, 479-485, 2000). WO 00/61194 discloses somatostatin peptide-dye conjugates used as contrast agents for optical diagnostics. WO 03/003806 discloses dye-azide compounds, including somatostatin ligands, for dual phototherapy of tumors and other lesions, while WO 03/004466 discloses dye-sulfenate derivatives and their bioconjugates for the same purposes.

U.S. Pat. No. 5,211,938 discloses a method of detection of malignant and non-malignant lesions by photochemotherapy of protoporphyrin IX precursors. JP 2000-342297 discloses cancer cell diagnosis by comparative genomic hybridization with fluorescent labeled probes.

Most of the present methods relating to cancer screening using fluorescence detection systems require the use of interventional devices such as endoscopes which have the special capability of delivering specified light frequencies to a targeted area within a patient. These endoscopes illuminate the targeted part of the body in which cancer is suspected. The light delivered at a specified frequency illuminates an area which has previously been subjected to some type of fluorescent marker, such as a porphyrin which causes malignant cells to illuminate or fluoresce under observation of light at a specified frequency. In these cases, introduction of an endoscope into the body requires some type of sedation or general or local anesthesia. Once a tumor has been located by use of the interventional device, depending upon the type of tumor, photochemotherapy or other treatment means can be used. However, prior to actual treatment, there must be a confirmed test of cancer. Accordingly, the tumor still needs to be sampled by an appropriate biopsy method that also require some type of sedation or anesthesia. Thus, traditional methods of confirming a malignancy may require at least two interventional surgical procedures. U.S. Pat. No. 6,316,215 discloses methods of cancer screening utilizing fluorescence detection techniques and selectable imager charge integration periods. The methods are claimed to allow a safe, reliable, inexpensive and minimally invasive diagnosis.

Photodynamic Therapy

An additional application for optically active receptor-targeted peptide conjugates is in photodynamic therapy (PDT). PDT is a medical technique used mainly for the ablation of cancer. In PDT, a patient is administered a PDT drug, and after the drug has accumulated in the tumor, the tumor is irradiated with light of a specific wavelength using a special light delivery system. Certain photo active molecules (most of them related to porphyrins), when irradiated with light of the proper wavelength in the presence of oxygen, generate reactive oxygen species (ROS) within the cancerous cell which kills the cell, and are therefore useful therapeutically in cancer. In the treatment of cancer, PDT combines light and endogenous oxygen with a photosensitizer localized in or around the tumor. Irradiation of the sensitizer produces a cascade of biochemical events that inactivate cancer cells either directly through attack at specific cellular sites or indirectly through the induction of vascular damage to blood vessels feeding the tumor.

Since many PDT drugs fluoresce at another, distinct wavelength, the same compounds can be used to image cancer using a special spectral imaging device. Spectral imaging can be used to locate a tumor for surgical resection, to locate residual tumor for resection control and to guide subsequent PDT. The therapeutic efficacy of PDT can be monitored in real time by fluorescence imaging during PDT. All of the above procedures are potentially achievable in the operating ward, endoscopically and externally.

An increasing number of regulatory-approved PDT procedures are being put into routine clinical practice. PDT has regulatory approval in the USA, Canada, The Netherlands, France, Germany, and Japan for cancers of the lung, digestive tract, and genitourinary tract. Photofrin® is also being evaluated as a protocol for treating cancers of the head and neck region and for treating pancreatic cancer as well as a possible therapy against Kaposi's sarcoma and cancers of the brain, breast (both primary and metastatic), skin, and abdomen. Although Photofri®n has been shown to be effective against a number of malignancies, it is not the "ideal" photosensitizer. Novel water-soluble porphyrins having improved properties were recently suggested. (Hilmey et al J. Med. Chem. 45, 449-461, 2002).

To date, PDT applications have employed non-receptor-targeted molecules that are taken up in cancer. The mechanisms by which cancer cells take up non-targeted PDT drugs are not well understood, and target to non-target ratios of PDT drug concentrations of only about 2-5 are obtained. There are few reports in the literature of PDT drug receptor targeted biomolecule conjugates demonstrating in vitro efficacy. De Luca et al. (J. Pep. Sci. 7, 386-394, 2001), described synthesis and characterization of a porphyrin-CCK8 conjugate in which the porphyrin is used as an indium chelator, but PDT is not mentioned. Del Govematore et al. (Cancer Res. 60, 4200-4205, 2000), demonstrated in vivo use of a chlorin-antibody construct for targeted PDT of colorectal cancer, but none of the background art publications disclose peptide-receptor-targeted in vivo PDT.

U.S. Pat. Nos. 5,308,608 and 5,149,708 disclose specific types of porphyrin compounds which may be used for detection, photosensitization, or the destruction of a targeted biological material when the targeted tissue is contacted with the specified porphyrin, and irradiated with light that excites the compound. WO 01/15694 and WO 00/41727 disclose methods and compounds for PDT of a target tissue using a light source that preferably transmits light to a treatment site transcutaneously. U.S. Pat. No. 6,054,449 discloses compounds and methods for PDT of intimal hyperplasia and other diseases. U.S. Pat. No. 6,333,319 discloses use of bacteriochlorophyll derivatives in PDT methods, while U.S. Pat. No. 6,147,195, U.S. Pat. No. 5,726,169, U.S. Pat. No. 5,955,585, and U.S. Pat. No. 5,650,292 disclose conjugates of chlorophyll and bacteriochlorophyll derivatives with peptides used as photosensitizers in photodynamic therapy and in diagnostics of tumors. U.S. Pat. No. 6,217,848 discloses cyanine and indocyanine dye-peptide, conjugates for diagnostic imaging and therapy, and specifically discloses somatostatin analogs useful for laser assisted guided surgery for the detection of small micrometastases tumors upon laparoscopy.

Improved Peptide Analogs

As a result of major advances in organic chemistry and in molecular biology, many bioactive peptides can now be prepared in quantities sufficient for pharmacological and clinical use. Thus in the last few years new methods have been established for the treatment and diagnosis of illnesses in which peptides have been implicated. However, the use of peptides as therapeutic and diagnostic agents is limited by the following factors: a) tissue penetration; b) low metabolic stability towards proteolysis in the gastrointestinal tract and in serum; c) poor absorption after oral ingestion, in particular due to their relatively high molecular mass or the lack of specific transport systems or both; d) rapid excretion through the liver and kidneys; and e) undesired side effects in non-target organ systems, since peptide receptors can be widely distributed in an organism.

It would be desirable to achieve peptide analogs with greater specificity thereby achieving enhanced clinical selectivity. It would be most beneficial to produce conformationally constrained peptide analogs overcoming the drawbacks of the native peptide molecules, thereby providing improved therapeutic properties.

A novel conceptual approach to the conformational constraint of peptides was introduced by Gilon et al. (Biopolymers 31:745, 1991) who proposed backbone-to-backbone cyclization of peptides. The advantages of this strategy include the ability to effect cyclization via the carbons or nitrogens of the peptide backbone without interfering with side chains that may be crucial for interaction with the specific receptor of a given peptide. Further disclosures by Gilon and coworkers (WO 95/33765, WO 97/09344, U.S. Pat. Nos 5,723,575, 5,811,392, 5,883,293 and 6,265,375), provided methods for producing building units required in the synthesis of backbone cyclized peptide analogs. The successful use of these methods to produce backbone cyclized peptide analogs of bradykinin (U.S. Pat. No. 5,874,529), and somatostatin (WO 98/04583, WO 99/65508, WO 99/65508, U.S. Pat. Nos. 5,770,687, 6,051,554, and 6,355,613) was also disclosed. WO 02/062819 discloses backbone cyclized radiolabelled SST analogs for radioimaging and therapy. All of these methods are incorporated herein in their entirety, by reference.

There remains a need for synthetic SST analogs having increased in vivo stability, to be used diagnostically and therapeutically, as agents labeled with photo-active moiety, for optical imaging in vivo, in vitro and ex vivo, and for therapeutic agents using photodynamic therapy. It would be desirable to achieve peptide analogs with greater specificity to receptor subtypes thereby achieving enhanced diagnostic selectivity to elucidate the specific SST receptor profile in each individual for planning further therapy and/or surgery. Backbone cyclized SST analogs that specifically fulfill these needs are provided by this invention. None of the background art teaches or suggests the photo-active labeled backbone cyclized somatostatin analogs disclosed herein having improved diagnostic and therapeutic activity and selectivity.

SUMMARY OF THE INVENTION

The present invention provides for the first time somatostatin receptor targeted backbone cyclized peptides conjugated to photo-active moieties for intraoperative diagnostic imaging and screening, photodynamic therapy and real-time monitoring of PDT efficacy.

According to one aspect of the present invention the novel photo-active somatostatin analogs provided are backbone cyclic peptide analogs having SST receptor subtype specific profiles may be used for individualizing the diagnosis and treatment of tumors by application of receptor-specific reagents.

Distinct from native SST and SST analogs known in the art, the cyclic peptides of the present invention are backbone cyclized SST analogs which possess unique and superior properties such as chemical and metabolic stability, selectivity, increased bioavailability and improved pharmacokinetics. These analogs are further labeled with photo-active moiety provided that the labeling methods and the conjugates maintain or increase the favorable properties of these backbone cyclic SST analogs in means of binding to specific somatostatin receptors.

According to another aspect of the present invention, novel photo-active-labeled peptide analogs which are characterized in that they incorporate building units with bridging groups attached to the alpha nitrogens of alpha amino acids, are disclosed. Specifically, these compounds are backbone cyclized somatostatin analogs comprising a peptide sequence of three to twenty four amino acids, each analog incorporating at least one building unit, said building unit containing one nitrogen atom of the peptide backbone connected to a bridging group comprising an amide, thioether, thioester, disulfide, urea, carbamate, or sulfonamide, wherein at least one building unit is connected via said bridging group to form a cyclic structure with a moiety selected from the group consisting of a second building unit, the side chain of an amino acid residue of the sequence or a terminal amino acid residue. Preferably, the peptide sequence incorporates 3 to 14 residues, more preferably 4 to 12 amino acids, most preferably 5-9 amino acids.

According to yet another aspect, the compounds of the present invention are backbone cyclized peptides conjugated to photo-active moieties upon stimulation with a predetermined wavelength of light fluorescent at one or more wavelength, or in addition to their ability to fluorescent at one or more wavelength generate reactive oxygen species at another wavelength (or other wavelengths), for the imaging and therapy of neoplasms and other disorders.

The main drawback of PDT as it is applied today is that the compounds used show low selectivity to the tumor tissue, resulting in damage to healthy tissue during irradiation and extended periods in which patients undergoing PDT must avoid exposure to light. The compounds of the present invention possess greatly enhanced tumor selectivity over the current commercially available drugs. The tumor-to-healthy tissue ratios achieved with non-targeted PDT drugs is 2-4 while the compounds of the present invention are expected to achieve ratios of 10-50 or more. Indeed, backbone cyclized radiolabelled somatostatin analogs (described in WO 02/062819), were shown to achieve somatostatin receptor targeting ratios as high as 47:1 (pancreas to muscle).

According to one embodiment, the backbone cyclized somatostatin analogs according to the present invention are covalently linked to a photo-active moiety via any free functional group available in the peptide. In most preferred analogs the photo-active moiety is covalently bound to the terminal nitrogen of the parent peptide. In other preferred analogs the photo-active moiety is covalently bound to the alpha amine of an C-terminal Lysine residue.

According to another embodiment of the present invention, preferred SSTR-targeting photo-active backbone cyclized somatostatin analogs possess suitable characteristics for intraoperative surgical guidance in the resection of neuroendocrine and other SSTR-expressing tumors, and in image guided receptor-targeted PDT of neuroendocrine and other SSTR-expressing tumors.

The present invention provides for the first time the possibility of obtaining a panel of backbone cyclized photo-active-labeled analogs with desired somatostatin receptor selectivity or with combinations of receptor selectivity. That enables diagnostic and therapeutic uses in different types of cancers and other diseases characterized with expression of somatostatin receptors, according to the specific needs of each patient and each disease.

According to another embodiment of the present invention, photo-active-labeled somatostatin analogs are analogs with improved affinity and selectivity to specific somatostatin subtypes. Specific embodiments provide novel backbone cyclic analogs of somatostatin which display receptor selectivity to SST-R subtypes 2, 5 or to SST-R subtypes 2 and 5. Other embodiments disclose analogs, which bind to more than two SST receptors. Another embodiment provides photo-active-labeled somatostatin analogs that may advantageously include bicyclic structures containing at least one cyclic structure connecting two building units and a second cyclic structure which is selected from the group consisting of side-chain to side-chain; backbone to backbone; and backbone to terminal.

The present invention provides compounds that when employed alone are formulated into pharmaceutical compositions for administration to the subject or applied to an in vitro target using techniques known in the art generally, are useful for diagnosis and treatment of cancerous and other diseases.

The pharmaceutical compositions comprising pharmacologically photo-active labeled backbone cyclized SST analogs and a pharmaceutically acceptable carrier or diluent represent another embodiment of the invention, as do the methods for the treatment of cancers in targeted photodynamic therapy using such compositions. The pharmaceutical compositions according to the present invention advantageously comprise at least one backbone cyclized peptide analog which is selective for one or more SST receptor subtype. These pharmaceutical compositions may be administered by any suitable route of administration, including orally, topically or systemically. Preferred modes of administration include but are not limited to parenteral routes such as intravenous, intracisternal, intraarterial and intramuscular injections, as well as via intra-nasal administration or oral ingestion.

The invention further provides a method for treating or diagnosing somatostatin-related diseases in animals, preferably humans, comprising administering a therapeutically effective amount of backbone cyclic SST analogs of the invention.

A non-limitative list of conditions and indications suitable for detection and treatment with the compounds of the present invention comprises: destruction of tumor tissue in solid tumors; treatment of topical conditions; systemic treatment of tumors and neoplastics such as bronchial, cervical, esophageal or colon cancer and for the diagnosis of same; esophageal and bladder cancers; treatment of superficial endobronchial nonsmall cell lung cancer (carcinoma in situ or microinvasive tumors) in patients for whom surgery and radiotherapy are not indicated; reduction of obstruction and palliation of symptoms in patients with completely or partially obstructing endobronchial nonsmall cell lung cancer; advanced form of Barrett's esophagus (a pre-cancerous condition which occurs when the lining of the esophagus converts to stomach-type tissue in response to chronic acid reflux, or heartburn); microinvasive (early) lung cancer; microinvasive endobronchial non-small cell lung cancer especially in patients who are not indicated for surgery and radiotherapy; advanced lung cancer; obstructive and partially obstructive esophageal cancer (palliation to improve swallowing); pre-cancerous skin lesions of the face or scalp called actinic keratoses; intimal hyperplasia; cancers of the head and neck region; pancreatic cancer; Kaposi's sarcoma; cancers of the brain, breast (both primary and metastatic), skin, and abdomen.

For diagnosis and treatment, the compounds according to the present invention may be used alone or may be further labeled with a radioisotope or other detecting or therapeutic means.

The present invention further provides backbone cyclized analogs that may be used as diagnostic compositions in methods for diagnosing cancer and imaging the existence of tumors or their metastases, and in detection of allograft rejection including but not limited to cardiac allograft rejection. The methods for diagnosis of cancer and allograft rejection comprise administering to a mammal, including a human patient, a backbone cyclic analog or analogs labeled with a detectable photo-active moiety. The methods for the diagnosis or imaging of cancer and allograft rejection using such compositions represent another embodiment of the invention.

According to another aspect of the invention the compounds are used to image cancer using a special spectral imaging device. Spectral imaging can be used to locate a tumor for surgical resection, to locate residual tumor for resection control and to guide subsequent PDT. The therapeutic efficacy of PDT can be monitored in real time by fluorescence imaging during PDT. All of the above procedures are potentially achievable in the operating ward, endoscopically and externally.

Another embodiment according to the present invention provides compounds and pharmaceutical compositions useful in genomic hybridization techniques and gene therapy applications in cells, which do not naturally express or do not adequately express somatostatin receptors, using a vector which carry the SST-R only or in addition to another therapeutic or diagnostic gene. Yet, another embodiment provides compounds that may be used for genetically modified cell-based therapy applying cells genetically modified to express SST-R (for imaging and/or therapy) alone or with other gene products.

The present invention further provides methods for administering to the subject a therapeutically effective amount of a targeted photosensitizing agent. This targeted substance preferably selectively binds to the target tissue, namely cells expressing somatostatin receptors. Light at a wavelength or waveband corresponding to that which is absorbed by the targeted substance is then administered. The light intensity is relatively low, but a high total fluoresce is employed to ensure the activation of the photosensitizing agent.

Some of the preferred analogs according to the present invention may comprise two or more isomers. The present invention includes such isomers either in combination or individually isolated.

According to a specific embodiment according to the present invention preferred photo-active moieties undergo fluorescent excitation and are able to fluoresce at a wavelength greater than 630 nm.

According to another embodiment of to the present invention, preferred photo-active moieties for PDT and real-time monitoring of PDT efficacy, are moieties which in addition to their ability to fluorescence at one distinct wavelength generate reactive oxygen species at another distinct wavelength. The wavelengths of fluorescent excitation, fluorescent emission or photodynamic excitation preferably are greater than or equal to 630 nm, allowing tissue penetration of light. Combination embodiments, wherein a particular complex is useful both in optical imaging and in photodynamic therapy, are also provided by the invention. Methods for making and using such backbone cyclic peptides, backbone cyclic reagents and photo-active labeled embodiments thereof are also provided.

The currently most preferred photo-active labeled backbone cyclized somatostatin analogs according to the present invention are now disclosed:

In preferred analogs according to the present invention the peptide is connected to the photo-active moiety via a linker to form a structure of the general Formula No. 1:

Z-Q-PTR                                             Formula No. 1 wherein Z is a photo-active moiety; Q is a direct bond or a linker moiety which can be connected to a free functional group of the peptide; and PTR denotes a backbone cyclized somatostatin.

Preferably Q comprises a covalent bond selected from the group consisting of amide, carbamate, urea, thiourea, amine, and sulfonamide; Z is selected from the group consisting of porphyrin derivatives, chlorin derivatives, bacteriochlorin derivatives, fluorescein derivatives, rhodamine derivatives, chlorophyll derivatives, and bacteriochlorophyll derivatives; and the somatostatin analog PTR is selected from the group of:

PTR 3207 having the structure DPhe-Cys*-Phe-Trp-DTrp-Lys-Thr-Phe-GlyS2*-NH$_2$(SEQ ID NO: 1);

PTR 3213 having the structure GlyS2*-Phe-Trp-DTrp-Lys-Thr-Phe-GlyS2*-NH$_2$(SEQ ID NO: 2);

PTR 3219 having the structure DPhe-GlyS2*-Phe-Trp-DTrp-Lys-Thr-Phe-GlyS2*-NH$_2$(SEQ ID NO: 3); and PTR 3173 having the structure GABA*-Phe-Trp-DTrp-Lys-Thr-Phe-GlyC3*-NH$_2$(SEQ ID NO: 4), The asterisks denote the cyclization points. The bridging group is connected between the $N^\alpha$-ω-functionalized derivative of the residue marked with one asterisk and free functional group of the second labeled residue or the second $N^\alpha$-ω-functionalized derivative.

Preferably, the linker Q is connected to the N-terminal of the peptide through an amide bond.

More preferably Q is selected from the group consisting of a direct bond, aminohexanoic acid, aminopentanoic acid, βAla, GABA and Gly; the photo-active moiety Z is selected from the group consisting of 5-(4-((oxocarbonyl)methyl)

phenyl)-10 ,15,20-triphenyl-21,23H-porphyrin; 5-(4-carboxyphenyl)-10,15,20-triphenyl-21,23H-porphyrin; 5-(4-((aminocarbonyl)methyl)phenyl)-10,15,20-triphenyl-21,23H-porphyrin; 5-(4-((oxocarbonyl)methyl)phenyl)-10,15,20-triphenyl-21,23H-chlorin (mixed isomers); 5-(aminothionyl)fluorescein; 4-sulfonyl-2sulfo-Lissamine™ rhodamine B; 2-sulfonyl-4-sulfo -Lissamine™ rhodamine B (mixed isomers); and 5- and 6-carboxyfluorescein (mixed isomers); and PTR is selected from the group consisting of:

PTR 3207 having the structure Dphe-Cys* -Phe-Trp-DTrp-Lys-Thr-Phe-GlyS2*-NH$_2$(SEQ ID NO: 1);

PTR 3213 having the structure GlyS2*-Phe-Trp-DTrp-Lys-Thr-Phe-GlyS2*-NH$_2$(SEQ ID NO: 2);

PTR 3219 having the structure Dphe-GlyS2*-Phe-Trp-DTrp-Lys-Thr-Phe-GlyS2* -NH$_2$ (SEQ ID NO: 3); and DesGABA-PTR 3173 having the structure Phe-Trp-DTrp-Lys-Thr-Phe-GlyC3* -NH$_2$.

The asterisks denote the cyclization points.

Other preferred compounds according to the present invention comprise photo-active backbone cyclized somatostatin analogs according to Formula No. 2:

Z-Lys(GABA-Phe-Trp-DTrp-Lys-Thr-Phe-Glyc3)-NH$_2$     Formula No. 2 wherein Z is a photo-active moiety connected to the alpha nitrogen of the C-terminal Lysine, and the peptide in parentheses is connected to the Lys epsilon amine and cyclized through an amide bond formed between the GABA terminal nitrogen and the Gly-C3 building unit carboxylate.

Preferably the photo-active moiety Z is a fluorescein derivative which is connected to the alpha nitrogen of the C-terminal Lysine through a bond selected from a thiourea or an amide bond.

The currently most preferred analogs according to the present invention are the compounds described in Table 1. These analogs were found to exhibit high affinity (in the 1-10 nanomolar range) to human SST-R2.

sequently selectively cyclizing the functional group with one of the side chains of the amino acids in the peptide sequence, with one of the peptide terminals, or with another ω-functionalized amino acid derivative.

Another aspect of the present invention provides methods for preparing photo-active labeled backbone cyclized analogs. Each such reagent comprises a backbone cyclized SST analog covalently linked to a photo-active moiety.

DETAILED DESCRIPTION OF THE INVENTION

Figure 1:
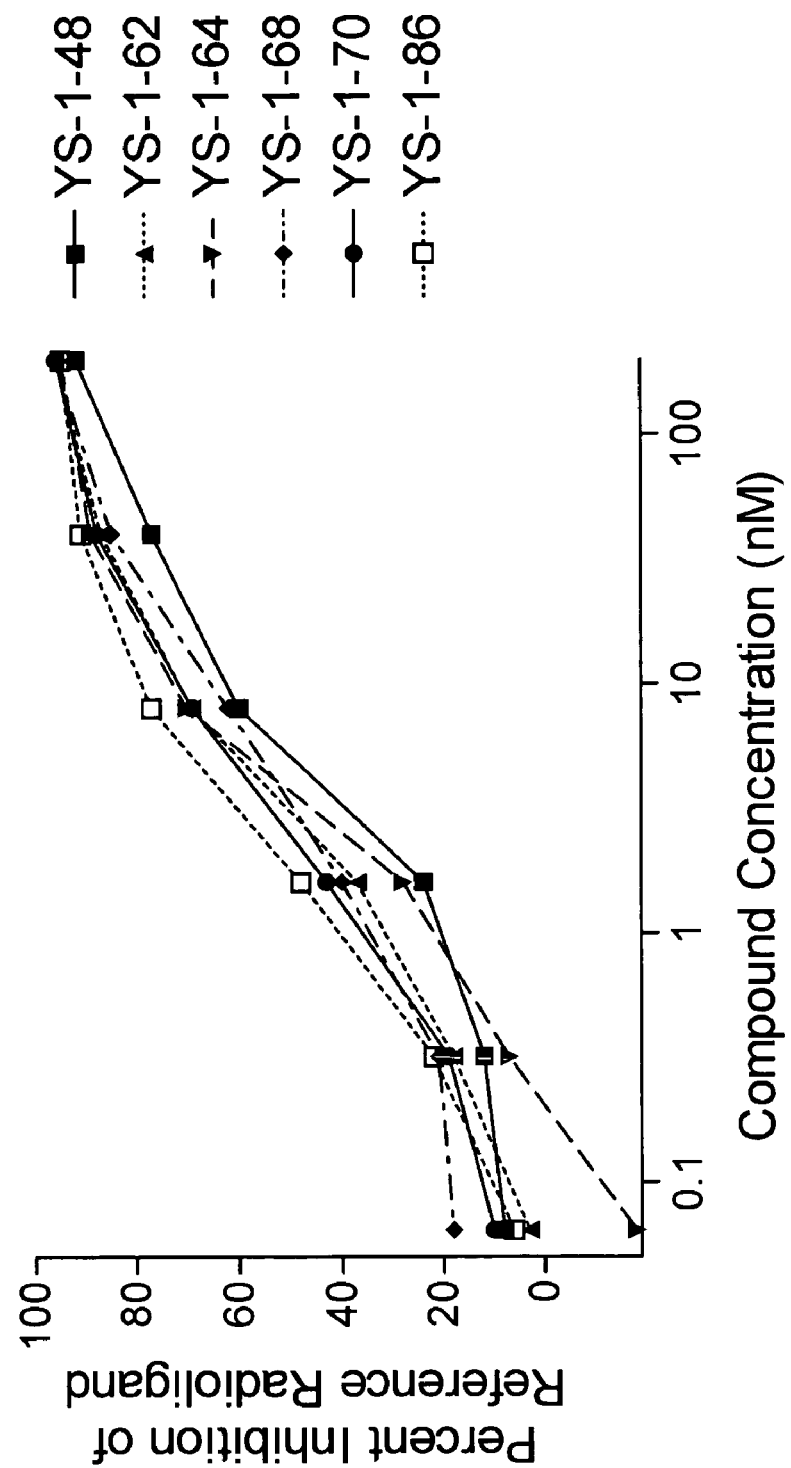
FIG. 1 describes the percent inhibition of SRIF-14 binding to hSST-R2 by selected photo-active backbone cyclized somatostatin analogs, as described in example 4.

According to the present invention, peptide analogs are cyclized via bridging groups attached to the alpha nitrogens of amino acids that permit novel non-peptidic linkages. In general, the procedures utilized to construct such peptide analogs from their building units rely on the known principles of peptide synthesis; most conveniently, the procedures can be performed according to the known principles of solid phase peptide synthesis.

The methods for design and synthesis of backbone cyclized analogs according to the present invention are dis-

TABLE 1

Most preferred photo-active backbone cyclized somatostatin analogs

| Peptide | Sequence |
|---|---|
| 1007A-01 | 5- and 6-carboxyfluorescein-Dab*-Phe-Trp-DTrp-Lys-Thr-Phe-GlyC3*-NH$_2$ |
| 1017A-01 | 5- and 6-carboxyfluorescein-Lys(GABA*-Phe-Trp-DTrp-Lys-Thr-Phe-GlyC3*)-NH$_2$ |
| YS-1-86 | 5-(aminothionyl)fluorescein-GABA-DPhe-Cys*-Phe-Trp-DTrp-Lys-Thr-Phe-GlyS2*-NH$_2$ |
| YS-1-70 | 5-(aminothionyl)fluorescein-aminopentanoyl-DPhe-GlyS2*-Phe-Trp-DTrp-Lys-Thr-Phe-GlyS2*-NH$_2$ |
| YS-1-62 | 5-(aminothionyl)fluorescein-β Ala-DPhe-GlyS2*-Phe-Trp-DTrp-Lys-Thr-Phe-GlyS2*-NH$_2$ |
| YS-1-64 | 5- and 6-carboxyfluorescein-β Ala-DPhe-GlyS2*-Phe-Trp-DTrp-Lys-Thr-he-GlyS2*-NH$_2$ |
| YS-1-48 | 5- and 6-carboxyfluorescein-GABA-GlyS2*-Phe-Trp-DTrp-Lys-Thr-Phe-GlyS2*-NH$_2$ |
| YS-1-68 | 5- and 6-carboxyfluorescein-GABA-DPhe-GlyS2*-Phe-Trp-DTrp-Lys-Thr-Phe-GlyS2*-NH$_2$ |

The asterisks denote the cyclization points. The bridging group is connected between the N$^\alpha$-ω-functionalized derivative of the residue marked with one asterisk and free functional group of the second labeled residue or the second N$^\alpha$-ω-functionalized derivative.

These backbone cyclized SST peptide analogs are prepared by incorporating at least one N$^\alpha$-ω-functionalized derivative of an amino acid into a peptide sequence and subclosed in U.S. Pat. Nos. 5,811,392; 5,874,529; 5,883,293; 6,051,554; 6,117,974; 6,265,375; 6,355,613, and international applications WO 95/33765; WO 97/09344; WO 98/04583; WO 99/31121; WO 99/65508; WO 00/02898; and WO 00/65467. All of these methods are incorporated herein in their entirety, by reference.

The most striking advantages of backbone cyclization are: 1) cyclization of the peptide sequence is achieved without compromising any of the side chains of the peptide thereby decreasing the chances of sacrificing functional groups essential for biological recognition (e.g. binding to specific receptors), and function; 2) optimization of the peptide conformation is achieved by allowing permutation of the bridge length, and bond type (e.g., amide, disulfide, thioether, thioester, urea, carbamate, or sulfonamide, etc.), bond direction, and bond position in the ring; 3) when applied to cyclization of linear peptides of known activity, the bridge can be designed in such a way as to minimize interaction with the active region of the peptide and its cognate receptor. This decreases the chances of the cyclization arm interfering with recognition and function, and also creates a site suitable for attachment of tags such as radioactive tracers, cytotoxic drugs, photo-active substances, or any other desired label.

Distinct from native SST and SST analogs known in the background art, the cyclic peptides of the present invention are backbone cyclized SST analogs which possess unique and superior properties such as chemical and metabolic stability, selectivity, increased bioavailability and improved pharmacokinetics. These analogs are further labeled with photoactive moieties provided that the labeling methods and the conjugates maintain or increase the favorable properties of these backbone cyclic SST analogs.

Terminology and Definitions

The term "analog of somatostatin" preferably means that the molecules are capable of mimicking at least one of the actions of somatostatin. The term "analog" further indicates a molecule that has the amino acid sequence according to the invention except for one or more amino acid changes. The design of appropriate "analogs" may be computer assisted. A peptide analog according to the present invention may optionally comprise at least one bond which is an amide-replacement bond such as urea bond, carbamate bond, sulfonamide bond, hydrazine bond, or any other covalent bond.

As used herein "peptide" indicates a sequence of amino acids linked by peptide bonds. Whenever "peptide of the invention" or "analogs of the invention" are mentioned in the present specification and claims, also salts and functional derivatives thereof are contemplated, as long as the biological activity of the peptide with respect to SST is maintained. Functional derivatives of the peptides of the invention covers derivatives which may be prepared from the functional groups which occur as side chains on the residues or the N- or C-terminal groups, by means known in the art, and are included in the invention as long as they remain pharmaceutically acceptable, i.e., they do not destroy the activity of the peptide. These derivatives may, for example, include aliphatic esters of the carboxyl groups, amides of the carboxyl groups produced by reaction with ammonia or with primary or secondary amines, N-acyl derivatives of free amino groups of the amino acid residues formed by reaction with acyl moieties (e.g., alkanoyl or carbocyclic aroyl groups) or O-acyl derivatives of free hydroxyl groups (for example those of seryl or threonyl residues) formed by reaction with acyl moieties. Salts of the peptides of the invention contemplated by the invention are physiologically acceptable organic and inorganic salts.

As used herein the term "backbone cyclic peptide" or "backbone cyclic analog" denote an analog of a linear peptide which comprising a peptide sequence of preferably 3 to 24 amino acids that incorporates at least one building unit, said building unit containing one nitrogen atom of the peptide backbone connected to a bridging group comprising an amide, thioether, thioester, disulfide, urea, carbamate, or sulfonamide, wherein at least one building unit is connected via said bridging group to form a cyclic structure with a moiety selected from the group consisting of a second building unit, the side chain of an amino acid residue of the sequence or a terminal amino acid residue. The asterisks represented in a backbone cyclic peptide formula denote the cyclization points. The bridging group is connected between the $N^\alpha$-ω-functionalized derivative of the marked residue and free functional group of that residue or the second $N^\alpha$-ω-functionalized derivative residue. More preferably, the peptide sequence incorporates 3-14 amino acids, still more preferably it incorporates 4-12 amino acids, and most preferably 5-9 amino acids.

A "building unit" indicates an $N^\alpha$ derivatized α amino acid of the general Formula No. 3:

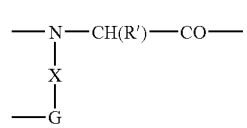

Formula No. 3 wherein X is a spacer group selected from the group consisting of alkylene, substituted alkylene, arylene, cycloalkylene and substituted cycloalkylene; R' is an amino acid side chain, optionally bound with a specific protecting group; and G is a functional group selected from the group consisting of amines, thiols, alcohols, carboxylic acids, sulfonates, esters, and alkyl halides; which is incorporated into the peptide sequence and subsequently selectively cyclized via the functional group G with one of the side chains of the amino acids in said peptide sequence, with one of the peptide terminals, or with another ω-functionalized amino acid derivative.

The methodology for producing the building units is described in international patent applications published as WO 95/33765 and WO 98/04583 and in U.S. Pat. Nos. 5,770, 687 and 5,883,293 all of which are expressly incorporated herein by reference thereto as if set forth herein in their entirety.

The building units are abbreviated by the three letter code of the corresponding modified amino acid followed by the type of reactive group (N for amine, C for carboxyl), and an indication of the number of spacing methylene groups. For example, GlyC2 describes a modified Gly residue with a carboxyl reactive group and a two carbon methylene spacer, and PheN3 designates a modified phenylalanine group with an amino reactive group and a three carbon methylene spacer. In generic formulae the building units are abbreviated as R with a superscript corresponding to the position in the sequence preceded by the letter N, as an indication that the backbone nitrogen at that position is the attachment point of the bridging group specified in said formulae.

The compounds herein disclosed may have asymmetric centers. All chiral, diastereomeric, and racemic forms are included in the present invention. Many geometric isomers of double bonds and the like can also be present in the compounds disclosed herein, and all such stable isomers are contemplated in the present invention. By "stable compound" or "stable structure" is meant herein a compound that is sufficiently robust to survive isolation to a useful degree of purity from a reaction mixture, and formulation into an efficacious diagnostic or therapeutic agent.

When any variable (for example R, X, Z, etc.) occurs more than one time in any constituent or in any Formula herein, its definition on each occurrence is independent of its definition at every other occurrence. Also, combinations of substituents and/or variables are permissible only if such combinations result in stable compounds.

The term "linker" denotes a chemical moiety whose purpose is to link, covalently, a photo-active moiety and a backbone cyclic peptide. The linker may be also used as a spacer whose purpose is to allow distance between the photo-active moiety and the backbone cyclic peptide.

The term "photo-active moiety" as used herein and in the claims is meant to encompass a moiety which upon stimulation with a predetermined wavelength of light emits fluorescence, or in addition to its ability to emits fluorescence generate reactive oxygen species.

A photo-active moiety emits fluorescence upon stimulation with a specific wavelength of light, wherein the predetermined wavelength can be absorbed by the targeted tissue and excites the compound's fluorophore causing it to fluoresce at an appropriate wavelength and intensity for detection, or excites the compound's photo-active moiety causing it to generate (in the presence of oxygen) the reactive oxygen species (ROS) for therapy.

The term "optical imaging agent" as used herein is meant to encompass a photo-active labeled agent capable of being detected with a detecting means (including but not limited to a cooled CCD camera) or device for use intraoperatively or otherwise in the detection of tumors, other tissue pathology or healthy tissue. The term "PDD" or "photodynamic diagnosis" as used herein is equivalent to the term optical imaging.

The term "PDT", "photo dynamic therapy", or "photodynamic therapy", as used herein is meant to encompass a method for treatment of pathologic tissue through administration of a photo-active labeled agent and irradiation of the tissue with light resulting in tissue ablation via generation of reactive oxygen species.

As used herein and in the claims, the phrase "therapeutically effective amount" means that amount of novel backbone cyclized peptide analog or composition comprising same to administer to a host to achieve the desired results for the indications disclosed herein, such as but not limited to cancer, endocrine disorders, inflammatory diseases, and gastrointestinal disorders.

Certain abbreviations are used herein to describe this invention and the manner of making and using it. For instance Alloc refers to allyloxycarbonyl, Boc refers to the t-butyloxy-carbonyl, Dab refers to diaminobutyric acid, DCM refers to dichloromethane, DIEA refers to diisopropyl-ethyl amine, DMF refers to dimethyl formamide, EDT refers to ethanedithiol, FOS refers to fiber-optic spectroscopic system, Fmoc refers to fluorenylmethoxycarbonyl, HOBT refers to 1-hydroxybenzotriazole, HPLC refers to high pressure liquid chromatography, GABA refers to gamma aminobutyric acid, MPS refers to Multiple parallel synthesis, MS refers to mass spectrometry, NMM refers to N-methylmorpholine, NMP refers to 1-methyl-2- -pyrolidonone, PDD refers to photodynamic diagnosis, PDT refers to photodynamic therapy, PEG refers to polyethylene glycol, PyBOP refers to benzotriazole-1-yl-oxy-tris-pyrrolidino-phosphonium hexafluorophosphate, PyBrOP refers to bromo-tris-pyrrolidino-phosphonium hexafluorophosphate, ROS refers to reactive oxygen species; RT refers to room temperature, SRIF refers to Somatotropin Release Inhibitory Factor, SST refers to somatostatin, SST-R refers to somatostatin receptor, tBu refers to the tertiary butyl, TFA refers to trifluoroacetic acid, TIS refers to triisopropylsilane.

The amino acids used in this invention are those which are available commercially or are available by routine synthetic methods. Certain residues may require special methods for incorporation into the peptide, and either sequential, divergent and convergent synthetic approaches to the peptide sequence are useful in this invention. Natural coded amino acids and their derivatives are represented by three-letter codes according to IUPAC conventions. When there is no indication, the L isomer was used. The D isomers are indicated by "D" or "(D)" before the residue abbreviation.

Conservative substitution of amino acids as known to those skilled in the art are within the scope of the present invention. Conservative amino acid substitutions includes replacement of one amino acid with another having the same type of functional group or side chain e.g. aliphatic, aromatic, positively charged, negatively charged. These substitutions may enhance oral bioavailability, penetration into the central nervous system, targeting to specific cell populations and the like. One of skill will recognize that individual substitutions, deletions or additions to peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Pharmacology

Apart from other considerations, the fact that the novel active ingredients of the invention are peptides or peptide analogs, dictates that the formulation be suitable for delivery of these type of compounds. Clearly, peptides are less suitable for oral administration due to susceptibility to digestion by gastric acids or intestinal enzymes. The preferred routes of administration of peptides are intra-articular, intravenous, intramuscular, subcutaneous, intradermal, or intrathecal. A more preferred route is by direct injection at or near the site of disorder or disease.

Pharmaceutical compositions of the present invention may be manufactured by processes well known in the art, e.g., by means of conventional mixing, dissolving, granulating, grinding, pulverizing, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active compounds into preparations which, can be used pharmaceutically. Proper formulation is dependent upon the route of administration chosen.

For injection, the compounds of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants for example polyethylene glycol are generally known in the art.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active compounds may be dissolved or suspended in suitable liquids, such as fatty oils, liquid paraff, or liquid polyethylene glycols. In addition, stabilizers may be added. All formulations for oral administration should be in dosages suitable for the chosen route of administration. For buccal administration, the compositions may take the form of tablets or lozenges formulated in conventional manner.

For administration by inhalation, the variants for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the peptide and a suitable powder base such as lactose or starch.

Pharmaceutical compositions for parenteral administration include aqueous solutions of the active ingredients in water-soluble form. Additionally, suspensions of the active compounds may be prepared as appropriate oily injection suspensions. Suitable natural or synthetic carriers are well known in the art (Pillai et al., Curr. Opin. Chem. Biol. 5, 447, 2001). Optionally, the suspension may also contain suitable stabilizers or agents, which increase the solubility of the compounds, to allow for the preparation of highly concentrated solutions. Alternatively, the active ingredient may be in powder form for reconstitution with a suitable vehicle, e.g., sterile, pyrogen-free water, before use.

The compounds of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of a compound effective to prevent, alleviate or ameliorate symptoms of a disease of the subject being treated. Determination of a therapeutically effective amount is well within the capability of those skilled in the art.

Toxicity and therapeutic efficacy of the peptides described herein can be determined by standard pharmaceutical procedures in cell cultures or experimental animals, e.g., by determining the $IC_{50}$ (the concentration which provides 50% inhibition) and the $LD_{50}$ (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition (e.g. Fingl, et al., 1975, in "The Pharmacological Basis of Therapeutics", Ch. 1 p.1).

Depending on the severity and responsiveness of the condition to be treated, dosing can also be a single administration of a slow release composition, with course of treatment lasting from several days to several weeks or until cure is effected or diminution of the disease state is achieved. The amount of a composition to be administered will, of course, be dependent on the subject being treated, the severity of the affliction, the manner of administration, the judgment of the prescribing physician, and all other relevant factors.

According to the present invention, novel peptide analogs which are characterized in that they incorporate novel building units with bridging groups attached to the alpha nitrogens of alpha amino acids, are disclosed. Specifically, these compounds are backbone cyclized somatostatin analogs comprising a peptide sequence of three to twenty four amino acids, each analog incorporating at least one building unit, said building unit containing one nitrogen atom of the peptide backbone connected to a bridging group comprising an amide, thioether, thioester, disulfide, urea, carbamate, or sulfonamide, wherein at least one building unit is connected via said bridging group to form a cyclic structure with a moiety selected from the group consisting of a second building unit, the side chain of an amino acid residue of the sequence or a terminal amino acid residue. Preferably, the peptide sequence incorporates 3 to 14 residues, more preferably 4 to 12 amino acids, most preferably 5-9 amino acids.

Backbone cyclic analogs of the present invention bind with high affinity to a defined subset of the human SST receptors. This receptor selectivity indicates the potential physiological selectivity in vivo. Furthermore, the present invention provides for the first time the possibility to obtain a panel of backbone cyclized photo-active labeled analogs with specific SST receptor selectivity or with combinations of receptor selectivity. This enables diagnostic and therapeutic uses in different types of cancers and other diseases according to the specific needs of each patient and each disease.

According to the present invention it is now disclosed that preferred SST analogs possess improved affinity and selectivity to specific SST subtypes. Preferred analogs include novel backbone cyclic analogs of SST which display receptor selectivity to SST-R subtypes 2, 5 or to SST-R subtypes 2 and 5. Other preferred analogs bind to more than two somatostatin receptors. Additional preferred SST analogs may advantageously include bicyclic structures containing at least one cyclic structure connecting two building units and a second cyclic structure which is selected from the group consisting of side-chain to side-chain; backbone to backbone and backbone to terminal.

The invention further provides backbone cyclic peptide reagents capable of being labeled with a photo-active moiety to form diagnostic and therapeutic agents, each comprising a backbone cyclized SST analog covalently linked to a photo-active moiety. According to the present invention the photo-active moiety can be linked to the analog in any free functional group available at the peptide. In most preferred analogs the photo-active moiety is covalently bound to the terminal nitrogen of the parent peptide directly or through a linker, or to the alpha nitrogen of a Lys residue.

The design of photo-active labeled compounds of the present invention was based on previously disclosed backbone cyclized somatostatin analogs characterized in their high affinity and selectivity to SST-R. It was demonstrated that backbone cyclized somatostatin analogs can be conjugated with relatively bulky fluorophores and the resulting conjugates could target hSSTR2. The synthesis of photo-active compounds was performed both in "Multiple-Parallel Synthesis" (MPS) format and in "batch" format. The compounds were first screened for their potency to bind the primary target receptor human SSTR subtype 2 (hSST-R2). Active compounds were now examined in vivo for their biodistribution in different tissues of NCI-H69 tumor-bearing nude mice.

Somatostatin is a tetradecapeptide hormone whose numerous regulatory functions are mediated by a family of five receptors, whose expression is tissue dependent. Receptor specific analogs of SST are believed to be valuable diagnostic and therapeutic agents in the treatment and diagnosis of various diseases. Attempts to design small peptide analogs having this selectivity have not been highly successful. It has now unexpectedly been found that the conformationally constrained backbone cyclized SST analogs of the present invention, are highly selective to SST receptor subtypes and are therefore useful for diagnosis and treatment of conditions where specific SST receptors are expressed in specific tissues. Such conditions are preferably different types of cancers such as colon cancer, growth hormone-secreting pituitary adenoma, thyroid cancer, gastric carcinoid, small cell lung carcinoma, melanoma, medullary non-Hodgkin's lymphoma, and breast cancer and other types of cancer. In addition, the backbone cyclized SST analogs of the present invention may be used for detection of allograft rejection including but not limited to cardiac allograft rejection.

Light sources for irradiation (and electronic excitation) of photo-active labeled SST analogs according to the present invention may be coherent (LASER) or non-coherent (conventional). In the case of coherent light, a diode is used to adjust the light wavelength for optimal irradiation of the optical imaging agent or PDT drug. In the case of non-coherent light, a filter is used to adjust the light wavelength. The optimal wavelength for imaging is that which electronically excites the compound's fluorophore causing it to fluoresce at an appropriate wavelength and intensity for detection which is preferably performed using by a cooled charged-coupled device (CCD) camera. The optimal wavelength for PDT according to the present invention is that which electronically excites the compound's PDT moiety causing it to generate (in the presence of oxygen) the reactive oxygen species (ROS) which is the therapeutic entity in PDT.

Photo-active moiety according to the present invention may be selected from any moiety known in the art, which is commercially available or in research or development. The most preferred photo-active moieties for optical imaging and PDT according to the present invention are selected form the group consisting of: fluorescein, Lissamine™ rhodamine B, porphyrins, chlorins, phthalocyanine, and indocyanine green. Additional preferred photo-active moieties are: hematoporphyrin derivative (HPD), phthalocyanine derivative (BPD), M-THPC (meta-tetrahydroxyphenylchlorin), 5,10,15,20-tetraarylethynylporphyrinatozinc(II), zinc phthalocyanine tetrasulfonate, tetraphenylporphyrins, porphycenes, porphyrinoids, porphyrin-diketones, deuteroporphyrin IX, hematoporphyrin, palladium (II) coproporphyrin I, and tetraarylethynylporphyrinatozinc(II) complexes.

Wherein a metal complex is possible for a photo-active backbone cyclic peptide analog, both the metal-free and the metal-containing moiety are included in the invention.

Backbone cyclized analogs of the present invention may be used as diagnostic compositions in methods for diagnosing cancer and imaging the existence of tumors or their metastases, and in detection of allograft rejection including but not limited to cardiac allograft rejection. The methods for diagnosis of cancer and allograft rejection comprise administering to a mammal, including a human patient, a backbone cyclic analog or analogs labeled with a detectable fluorophore. The methods for the diagnosis or imaging of cancer and allograft rejection using such compositions represent another embodiment of the invention.

The imaging agents provided by the invention have utility for tumor imaging, particularly for imaging primary and metastatic neoplastic sites wherein said neoplastic cells express SST receptors, and in particular such primary and especially metastatic tumor cells that have been clinically difficult to detect and characterize using conventional methodologies. The imaging reagents according to the present invention may be used for visualizing organs, and tumors, in particular gastrointestinal tumors, myelomas, small cell lung carcinoma and other APUDomas, endocrine tumors such as medullary thyroid carcinomas and pituitary tumors, brain tumors such as meningiomas and astrocytomas, and tumors of the prostate, breast, colon, and ovaries can also be imaged.

The compounds according to the present invention may be administered using any type of administration route known in the art. The photo-active labeled diagnostic reagents are preferably administered intravenously in a single unit injectable dose in any conventional medium for intravenous injection such as an aqueous saline medium. Other preferred administration route is topical application used especially in treating and diagnosing skin lesions and various cancer types (e.g. BCC, melanoma). Subcutaneous administration of the compounds and pharmaceutical compositions according to the present invention is preferably preformed in abdominal, head and neck tumors and similar tumors. Intraoperative application may be preferably used following tumor removal/debulking, for resection control (PDD), PDT ablation of residual tumor (particularly small tumors) or adjuvant PDT. Endoscopic application is preferably used for tumors of lung, trachea (respiratory system, plus nasal passages and sinuses); mouth, esophagus, stomach, colon, rectum (gastrointestinal system); gynecological system, urinary/bladder/prostate; general/minimally invasive surgery.

Excitation light application and optical imaging are preferably topical, subcutaneous (through the skin to relatively deep levels with highly penetrating excitation and emission light—i.e. near infrared, intraoperative or endoscopic.

The pharmaceutical compositions comprising pharmacologically active backbone cyclized SST analog and a pharmaceutically acceptable carrier or diluent represent another embodiment of the invention, as do the methods for the treatment of cancers in targeted PDT using such compositions. The pharmaceutical compositions may be administered by any suitable route of administration, including orally, topically or systemically. Preferred modes of administration include but are not limited to parenteral routes such as intravenous and intramuscular injections, as well as via intra-nasal administration or oral ingestion. The preferred doses for administration of such pharmaceutical compositions range from about 0.1 µg/kg to about 20 mg/kg body weight/day.

The pharmaceutical compositions according to the present invention are useful in the treatment of selected target tissues applying transcutaneous PDT, such as vascular endothelial tissue, the abnormal vascular walls of tumors, solid tumors of the head and neck, tumors of the gastrointestinal tract, tumors of the liver, tumors of the breast, tumors of the prostate, tumors of the lung, nonsolid tumors, malignant cells of the hematopoietic and lymphoid tissue and other lesions in the vascular system or bone marrow, and tissue or cells related to autoimmune and inflammatory disease.

If the treatment is to be localized, such as for the treatment of superficial tumors or skin disorders, the active conjugates may be topically administered using standard topical compositions involving lotions, suspensions, or pastes.

The pharmaceutical compositions may preferably be used to promote regression of certain types of tumors, particularly those that express SST receptors. Furthermore, the pharmaceutical compositions can also be used to reduce the hormonal hypersecretion that often accompanies certain cancers, such as the APUDomas. Other conditions of which the compounds of the present invention are useful for treatment are endocrine disorders, gastrointestinal disorders, diabetes-associated complications, pancreatitis, autoimmune diseases, and inflammatory diseases, allograft rejection, atherosclerosis and restenosis.

The invention further provides a method for alleviating somatostatin-related diseases in animals, preferably humans, comprising administering a therapeutically effective amount of photo-active labeled backbone cyclic SST analogs of the invention to the animal.

The compounds and the pharmaceutical compositions according to the present invention may be further used in gene therapy in which a gene is (or multiple genes are) targeted to any cell (for example cancer). The targeting vector can carry the SST-R gene only; in such case expressed SST-R can be used for both imaging and therapy. The vector can carry both the SST-R gene and another gene; in such case expressed SST-R can be used for imaging while the second gene product would be used for therapy. In general, SST-R-targeted optical imaging agents would be used to determine whether the gene therapy was successful. After confirmation that the gene has reached the target and is being expressed as a gene product (through SST-R imaging), therapy would commence (whether utilizing the SST-R or the second gene product).

Additional application of the compounds and the pharmaceutical compositions according to the present invention is genetically modified cell based therapy in which, similar to gene therapy, cells (stem or other) can be genetically modified to express SST-R (for imaging and/or therapy) alone or with other gene products (for therapy). Imaging the genetically modified cells would help in understanding whether the cells reached the target.

Another aspect of the present invention provides methods for preparing PDD and PDT agents and the reagents required for making them. Each such reagent comprises a backbone cyclized SST analog covalently linked to a photo-active moiety.

Preferred Embodiments

The most preferred backbone cyclized SST analogs according to the present invention are now disclosed:

In preferred analogs according to the present invention the peptide is connected to the photo-active moiety via a linker to form a structure of the general Formula No. 1:

Z-Q-PTR                    Formula No. 1 wherein Z is a photo-active moiety; Q is a direct bond or a linker moiety which can be connected to a free functional group of the peptide; and PTR denotes a backbone cyclized somatostatin analog.

Preferably Q comprises a covalent bond selected from the group consisting of amide, carbamate, urea, thiourea, amine, and sulfonamide; Z is selected from the group consisting of porphyrin derivatives, chiorin derivatives, bacteriochiorin derivatives, fluorescein derivatives, rhodamine derivatives, chlorophyll derivatives, and bacteriochlorophyll derivatives; and the somatostatin analog PTR is selected from the group of:

PTR 3207 having the structure Dphe-Cys*-Phe-Trp-DTrp-Lys-Thr-Phe-GlyS2*-NH$_2$(SEQ D NO: 1);

PTR 3213 having the structure GlyS2*-Phe-Trp-DTrp-Lys-Thr-Phe-GlyS2*-NH$_2$(SEQ ID NO: 2);

PTR 3219 having the structure Dphe-GlyS2*-Phe-Trp-DTrp-Lys-Thr-Phe-GlyS2* -NH$_2$ (SEQ ID NO: 3); and PTR 3173 having the structure GABA *-Phe-Trp-DTrp-Lys-Thr-Phe-GlyC3*-NH$_2$(SEQ ID NO: 4).

The asterisks denote the cyclization points. The bridging group is connected between the N$^\alpha$-ω-functionalized derivative of the residue marked with one asterisk and free functional group of the second labeled residue or the second N$^\alpha$-ω-functionalized derivative.

Preferably, the linker Q is connected to the N-terminal of the peptide through an amide bond.

More preferably Q is selected from the group consisting of a direct bond, aminohexanoic acid, aminopentanoic acid, βAla, GABA and Gly; the photo-active moiety Z is selected from the group consisting of 5-(4-((oxocarbonyl)methyl) phenyl)-10,15,20-triphenyl-21,23H-porphyrin; 5-(4-carboxyphenyl)-10,15,20-triphenyl-21,23H-porphyrin; 5-(4-((aminocarbonyl)methyl)phenyl)-10,15,20-triphenyl-21,23H-porphyrin; 5-(4-((oxocarbonyl)methyl)phenyl)-10,15,20-triphenyl-21,23H-chlorin (mixed isomers); 5-(aminothionyl) fluorescein; 4-sulfonyl-2sulfo-Lissamine™ rhodamine B; 2-sulfonyl-4-sulfo -Lissamine™ rhodamine B (mixed isomers); and 5- and 6-carboxyfluorescein (mixed isomers); and PTR is selected from the group consisting of:

PTR 3207 having the structure Dphe-Cys*-Phe-Trp-DTrp-Lys-Thr-Phe-GlyS2*-NH$_2$(SEQ ID NO: 1);

PTR 3213 having the structure GlyS2*-Phe-Trp-DTrp-Lys-Thr-Phe-GlyS2*-NH$_2$(SEQ ID NO: 2);

PTR 3219 having the structure Dphe-GlyS2*-Phe-Trp-DTrp-Lys-Thr-Phe-GlyS2* -NH$_2$ (SEQ ID NO: 3); and DesGABA-PTR 3173 having the structure Phe-Trp-DTrp-Lys-Thr-Phe-GlyC3* -NH$_2$.

The asterisks denote the cyclization points.

Other preferred compounds according to the present invention comprise photo-active backbone cyclized somatostatin analogs according to Formula No. 2:

Z-Lys(GABA-Phe-Trp-DTrp-Lys-Thr-Phe-GlyC3)-NH$_2$                Formula No. 2 wherein Z is a photo-active moiety connected to the alpha nitrogen of the C-terminal Lysine, and the peptide in parentheses is connected to the Lys epsilon amine and cyclized through an amide bond formed between the GABA terminal nitrogen and the Gly-C3 building unit carboxylate.

Preferably the photo-active moiety Z is a fluorescein derivative which is connected to the alpha nitrogen of the C-terminal Lysine through a bond selected from a thiourea or an amide bond.

These backbone cyclized SST peptide analogs are prepared by incorporating at least one N$^\alpha$-ω-functionalized derivative of an amino acid into a peptide sequence and subsequently selectively cyclizing the functional group with one of the side chains of the 5 amino acids in the peptide sequence or with another (ω-functionalized amino acid derivative.

Table 2 describes some of the preferred analogs of the present invention and their affinity for the hSST-R2.

TABLE 2

| Peptide | Sequence | IC$_{50}$ nM |
|---|---|---|
| 1007A-01 | 5- and 6-carboxyfluorescein-Dab*-Phe-Trp-DTrp-Lys-Thr-Phe-GlyC3*-NH$_2$ | 78 |
| 1017A-01 | 5- and 6-carboxyfluorescein-Lys(GABA*-Phe-Trp-DTrp-Lys-Thr-Phe-GlyC3*)-NH$_2$ | 13.2 |
| YS-1-86 | 5-(aminothionyl)fluroescein-GABA-DPhe-Cys*-Phe-Trp-DTrp-Lys-Thr-Phe-GlyS2*-NH$_2$ | 1.7 |
| YS-1-70 | 5-(aminothionyl)fluorescein-aminopentanoyl-DPhe-GlyS2*Phe-Trp-DTrp-Lys-Thr-Phe-GlyS2*-NH$_2$ | 2.9 |
| YS-1-62 | 5-(aminothionyl)fluorescein-βAla-DPhe-GlyS2*-Phe-Trp-DTrp-Lys-Thr-Phe-GlyS2*-NH$_2$ | 3.0 |
| YS-1-64 | 5- and 6-carboxyfluorescein-βAla-DPhe-GlyS2*-Phe-Trp-DTrp-Lys-Thr-Phe-GlyS2*-NH$_2$ | 3.9 |
| YS-1-48 | 5- and 6-carboxyfluorescein-GABA-GlyS2*-Phe-Trp-DTrp-Lys-Thr-Phe-GlyS2*-NH$_2$ | 5.4 |
| YS-1-68 | 5- and 6-carboxyfluorescein-GABA-DPhe-GlyS2*-Phe-Trp-DTrp-Lys-Thr-Phe-GlyS2*-NH$_2$ | 5.7 |

The asterisks denote the cyclization points.

As shown, the affinity of the preferred analogs to type 2 SST receptor is in the nanomolar to tens of nanomolar range which makes these analogs potentially effective diagnostic and therapeutic compositions.

General Method for Synthesis, Purification and Characterization of Backbone Cyclic Peptides Synthesis:

Resin: 1 g Rink amide or Tenta-gel resin, with loading of 0.2-0.7 mmol/g.

Fmoc-deprotection: With 7 mL of 20% piperidine in NMP (twice for 15 minutes). Followed by 5 washes with 10 mL NMP for 2 minutes with shaking.

Couplings:
1. Regular couplings (coupling to simple amino acids): with a solution containing 3 equivalents amino acid, 3 equivalents PyBroP and 6 equivalents of DEA in 7 mL NMP. For 0.5-2 hours with shaking. Coupling is monitored by ninhydrin test and repeated until the ninhydrin solution remains yellow.
2. Coupling of His and Asn with a solution containing 5 equivalents DIC and 5 equivalents HOBT in 10 mL DMF.
3. Coupling to Gly building units: with a solution containing 3 equivalents amino acid, 3 equivalents PyBroP and 6 equivalents DIEA in 7 mL NMP. Twice for 1-4 hours with shaking.
4. Coupling to building units other than Gly: with a solution containing 5 equivalents amino acid, 1.5 equivalents triphosgene and 13 equivalents collidine in 15 mL dioxane or tetrahydrofuran. Twice for 0.5-2 hours at 50° C. with shaking.

Removal of the Allyl and Alloc protecting groups of the building units: with 0.6 equivalent per Allyl or Alloc of Pd(PPh$_3$)$_4$ in 30 mL DCM containing 5% acetic acid and 2.5% NMM. For 1-4 hours with shaking.

Cyclization: with a solution containing 3 equivalents PyBOP and 6 equivalents DIEBA in 7 mL NMP. For 0.5-2 hours with shaking. Cyclization is monitored by ninhydrin test and repeated if necessary.

Cleavage: with 82%-95% TFA supplemented with scavengers: 1-15% H$_2$O, 1-5% TIS and O-5% EDT.

Purification:

An individual purification method for each backbone cyclic peptide is developed on analytical HPLC to optimize isolation of the cyclic peptide from other components. The analytical method is usually performed using a C-18 Vydac column 250×4.6 mm as the stationary phase and water/acetonitrile containing 0.1% TFA mixture gradient. The preparative method is designed by adapting the analytical separation method to the preparative C-18 Vydac column. During the purification process, the peak containing the cyclic peptide is collected using a semi-automated fraction collector. The collected fractions are injected to the analytical HPLC to check purity. The pure fractions are combined and lyophilized.

Characterization:

The combined pure lyophilized material is analyzed for purity by HPLC, MS and capillary electrophoresis and by amino acid analysis for peptide content and amino acid ratio determination.

General Method for Synthesis, Purification and Characterization of Libraries in Multiple Parallel Synthesis (MPS) Format:

The MPS procedure is used as the routine peptide development procedure. Individual peptides, or groups of a few peptides, are synthesized in 96-wells microtiter plates equipped with filters that allow passage of solvent but not of solid phase matrix. A simple and efficient valve apparatus that enables simultaneous closing and opening of all the valves (produced by Millipore) is used. The system utilizes an approach in which each well is equipped with a solvent permeable membrane at the bottom that does not pass particles above a certain size. The process allows one to place resin in the wells, perform reaction in solvent, and remove the solvent from all the wells simultaneously by applying vacuum. These special plates, which are available in the standard 96 well format allow the parallel synthesis of 96 peptides simultaneously. The synthetic scale of the procedure is in the range of 1-5 μmole per well. Following purification by C18 reverse phase columns (SepPak or semi-preparative Vydac), which is also carried out in the standard 96 well format, the peptides are routinely dissolved in 1 ml of water to yield a theoretical crude concentration of 1-5 mM (depending of synthesis scale). Monitoring of chemical quality of the resulting peptides is performed by ESI-MS analysis. Analysis of several plates prepared on different occasions by different operators indicated a general success rate of about 80% as judged by the presence of the desired peptide mass in the crude preparation. Further analysis of a peptides from MPS is carried out by LC-MS. The analysis revealed crude peptide quality similar to crude preparations of peptides synthesized individually in large scale. Individual steps or the complete process is now performed automatically using automatic peptide synthesizers. According to the present exemplifications, the peptides are currently synthesized automatically using the ACT 396 and VANTAGE of Advanced ChemTech, and the heating device Lab Tech 4 of Advanced ChemTech.

Detailed Procedure for Synthesis in MPS Format:
For capacity of 6 µmole, 10 mg resin with a substitution of 0.6 mmol/gr is used.
Fmoc deprotection: To each well 500 µl of 5% piperidine in NMP is added twice. The mixture is shaken for 15 min. The NMP is removed by suction.
Washing after Fmoc deprotection: the resin is washed by placing 600 µl NMP into each well followed by evacuation of the solution by a stream of nitrogen. The washing process is repeated 4 times.
Coupling Using HBTU:
Well capacity: 6 µmol
Amount of amino acid per coupling per well: 30 µmol
Amino acid in NMP concentration: 0.2 M
Amino acid volume used: 150 µl
HBTU amount: 30 µmol
HBTU concentration: 0.2 M
HBTU volume used: 150 µl
DIEA added: 150 µl of 0.4 M in NMP
Total reaction volume: 450 µl The amino acids are dissolved in a solution of HOBT in NMP. The resin is washed by placing 600 µl NMP into each well followed by evacuation of the solution by steam of nitrogen. The washing process is repeated 4 times. The coupling reaction is repeated twice for 1 hour.
Coupling Using Mukavama Reagent (Performed Only in Certain Situations):
Amino acid solution at 650 mM-40 µl
Mukayama reagent at 111 mg/ml-60 Li Collidine added per well-15 µl The same procedure as for coupling with PyBroP. Reaction temperature 50° C., reaction time: first coupling 4 h, second coupling 16 h.
Allyl Alloc deprotection: is performed after completing the assembly, by addition of 180 µl solution of 1.5 g Pd(PPh$_3$)$_4$ in 20 ml CH$_2$Cl$_2$ containing 5% acetic acid+2.5% NMM.
Cyclization: this step is performed by addition of 100 µl of PyBoP in NMP+DIEA.
Cleavage of the peptide from the resin and SepPak purification: After final Fmoc deprotection the resin is transferred into a deep well microtiter plate, to each well 300 µl of TFA solution containing 2.5% TIS, 2.5% H$_2$O, 2.5% EDT are added. Removal of the TFA is performed by lyophilization. After cleavage the peptides are purified by SepPak.

General Method for In Vitro Screening of Somatostatin Analogs
The ability of the SST analogs of the invention to bind to SST receptors in vitro was demonstrated by assaying the ability of such analogs to inhibit binding of a radiolabelled SST analog to SST receptor-containing cell membranes. The SST analogs were tested for their potency in inhibition of the binding of $^{125}$I-Tyr$^{11}$-SRIF (based on the method described by Raynor et. al., Molecular Pharmacology 43: 838, 1993) to membrane preparations expressing transmembrane SST receptors (SST-R1, 2, 3, 4 or 5). The receptor preparations used for these tests were either from the cloned human receptors selectively and stably expressed in Chinese Hamster Ovary (CHO) cells or from cell lines naturally expressing the SST-Rs. Typically, cell membranes were homogenized in Tris buffer in the presence of protease inhibitors and incubated for 30-40 minutes with $^{125}$I-Tyr$^{11}$-SRIF with different concentrations of the tested sample. The binding reactions were filtered, the filters were washed and the bound radioactivity was counted in P counter after addition of scintillation solution. Non specific binding was defined as the radioactivity remaining bound in the presence of 1 µM unlabeled SRIF-14.

In Vitro Biological Characterization Assays
A number of in vitro biological experiments are performed to fully characterize the conjugates. In these experiments, the molecule's fluorescence is used for quantitative measurements of parameters (a fluorimetric assay). Anywhere a cell assay is indicated, a cell membrane assay could also be performed (except for internalization). Cell uptake kinetics ($k_{on}$ and $k_{off}$, ligand "on rate" and "off rate," respectively) is measured in CHO cells transfected with hSSTR1-5, AR42J cells and NCH-H69 cells. These numbers are used to calculate each compound's $K_d$ or equilibrium dissociation constant. A saturation experiment (i.e., generation of a "scatchard plot") is performed in order to measure specific binding (and $K_d$ in another way). Competitive binding studies are performed for each ligand versus SRIF, Sandostatin and other SST-R ligands of interest. Conjugate internalization is studied by incubating the cells with varying concentrations of conjugate. Internalization is important since it greatly increases the conjugate's cellular residence time and internalization should direct the ROS to destroy intracellular components, possibly making PDT more effective. Conjugates that show higher levels of internalization would be expected to perform better in vivo. Additionally, the in vivo optimal dose might be predicted through determination of optimal internalization concentrations.

In vitro PDT studies are performed taking into consideration the optimal wavelength for PDT and the optimal concentration for internalization. Cells are incubated in PDT conjugate (in some cases, subsequently washed to eliminate PDT conjugate from the medium) and irradiated with light. Cell survival is then measured versus controls (no conjugate, no light).

Physical Characterization of Photo-Active Labeled Compounds
In vitro spectroscopic (or "photo physics") characterization include measurement of each compound's:
i. absorbance wavelength spectrum;
ii. molar absorptivity coefficients at select absorbance wavelength maxima;
iii. fluorescence emission spectra (at selected excitation wavelengths);
iv. fluorescence quantum yield (at selected wavelengths);
v. rate of photobleaching; and
vi. for PDT compounds, ROS generation efficiency (singlet oxygen quantum yield).

Optical Imaging Methods

Fiber-optic Spectrofluorimetry
An argon ion laser (Melles Griot, 43 series) was coupled to a spectrofluorophotometer (Shimadzu, model RF-5301PC) using a bifurcated fiber bundle (Oriel, Stratford, Conn., model 77533). Laser light (488 nm) was passed via one leg of the fiber bundle, the common end tip of the bundle was fixed at a distance of 1 mm from a tissue sample, while the end tip of the second leg was mounted in front of the entrance slit of the spectrofluorophotometer. Laser irradiation from the fiber was set to 5 mW, as measured with a laser power meter (Laserstar, Ophir, Israel). An average of three recordings was used for each data point.

Fluorescence Imaging

A Spectral Image-analysis system (SpectraCube™ SD 300, Applied Spectral Imaging, Migdal Ha'Emek, Israel) was used for fluorescence imaging. The system combines conventional imaging with Fourier transform spectroscopy. Briefly, light emitted from an object is collected and collimated by an optical objective. The beam is spectrally dispersed passing through a Sagnac (triangular) common path interferometer and is imaged by a focusing lens on a 1280×1024 CCD array of a high-resolution digital camera. Each pixel of the CCD image collects an interferogram, which is subsequently Fourier transformed to give the spectrum of that pixel. During a measurement, all spectra are obtained simultaneously and stored in a file. The spatial resolution, depending on the objective lenses in use, was better than 0.1 mm. The spectral range (more than 5% response) is 400-1000 nm and at 600 nm the spectral resolution is better than 5 nm.

In Vivo Assays

Biodistribution assays are performed by first injecting the photo-active conjugate and then following its in vivo biodistribution through excitation (by either a coherent or non-coherent light source) and cooled CCD camera imaging. Animals' models can be the normal rat (in which SSTR target organs are the pancreas and adrenals) or a rat or mouse (normal or immune deficient) bearing a tumor that expresses SST-R. These studies are performed in surgery (intraoperatively) or in intact animals.

In vivo PDT is performed in animals bearing a tumor that expresses SST-R. Animals are injected with the PDT conjugate and after a wait time (predetermined in a biodistribution experiment or measured through optical imaging during the PDT study), PDT irradiation of the tumor will commence. A degree of PDT control is achieved by alternatively irradiating the tumor for PDT and fluorescence imaging the tumor to determine the amount of non-photobleached drug remaining. Success of the PDT is determined by measurement of tumor size reduction and animal survival time versus controls (no treatment, no light, no conjugate).

In Vivo Models for Evaluating the Activity of Somatostatin Analogs

The photo-active labeled compounds of the present invention are tested in vivo for tumor uptake in xenografts derived from cell lines such as the following:
a. Rat pituitary adenoma cells (GH3) in nude rats.
b. Human colon adenocarcinoma cells (HT-29) in nude mice or nude rats.
c. Rat pancreatic acinar carcinoma cells (CA20948) in normal rats.
d. Rat pancreatic cancer cells (AR42J) in nude mice.
e. Human small cell lung carcinoma cells (NCI-H69) in nude mice.
f. Human pancreatic carcinoid cells (BON-1) in nude mice or nude rats.
g. LCC-18 cells in nude mice or nude rats.
h. DSL 62-38 cell line in normal or nude rats or in nude mice.

Briefly, the cells are implanted intramuscularly in a suspension of 0.05 to 0.1 mL/animal, the tumors are allowed to grow to approximately 0.5 to 2 g, harvested, and used to implant a second, naive set of animals. Passaging in this fashion is repeated to generate successive generations of tumor-bearing animals. Third- to fifth-passage of tumor-bearing animals are injected intravenously with labeled compound. Alternatively, the tumor bearing animals are those that grow tumors after injection of cells from in vitro culture. Tumors with surface dimensions of about 0.5×0.5 cm are adequate for in vivo use.

Additional in vivo models for imaging of SST receptors expressed by animal tumor cells are performed essentially as described by Achilefu et al. ibid. and Becker et al. Nat. Biotechnol. 19, 327-31, 2001.

Conformationally constrained SST analogs constructed based in part on the sequences of a number of known biologically active peptides or based on previously unknown novel sequences are presented in the examples below. The following examples are intended to illustrate how to make and use the compounds and methods of this invention and are in no way to be construed as a limitation. Although the invention will now be described in conjunction with specific embodiments thereof, it is evident that many modifications and variations will be apparent to those skilled in the art. Accordingly, it is intended to embrace all such modifications and variations that fall within the spirit and broad scope of the amended claims.

EXAMPLES

The invention will now be illustrated in a non-limitative manner by the following Examples:

Example 1

Detailed Procedure of PTR-1017A Synthesis

Rink amide MBHA resin (1 g, 0.5 mmol) was swelled in NMP (4 h) in a glass reactor equipped with a sintered glass bottom. Fmoc was removed from the resin using two 15-min piperidine-NMP (1:3, 10 mL) treatments. After washing the resin thoroughly (NMP, 7×, 10 mL, 2 min), DDE-Lys(Fmoc) OH (2 mmol) was coupled in NMP (10 mL) with PyBroP (2 mmol) and DIEA (4 mmol) as activating agents (1 h, RT). Following coupling, the modified resin was washed (NMP, 5×, 10 mL, 2 min). Reaction completion was checked by a qualitative ninhydrin (Kaiser) test. Fmoc removal and subsequent washing was carried out as described above, followed by washing with DCM (3×, 10 mL, 2 min). Fmoc-GlyC3-OH (2.0 mmol) was coupled to the epsilon-nitrogen on the lysine residue using the same NMP/PyBroP/DIEA method described above. Successive addition of Fmoc-Phe-OH, Fmoc-Thr(tBu)-OH, Fmoc-Lys(Boc)-OH, Fmoc-(D)Trp (Boc)-OH, Fmoc-Trp(Boc)-OH, Fmoc-Phe-OH and Fmoc-GABA(Alloc)-OH was accomplished using standard coupling cycles as described above. After washing the peptidyl resin with DCM (3×, 10 mL, 2 min), Allyl/Alloc deprotection was achieved by adding Pd(P(Ph)$_3$)$_4$ (1 g) in chloroform-acetic acid —NMM (67:2:1, 10.5 mL, argon-sparged) to the reactor, degassing by bubbling argon through the reactor's sintered glass bottom and then shaking vigorously for 1.5 h in the dark. The cyclic peptidyl resin was washed thoroughly with DCM and NMP. Backbone cyclization was accomplished using HATU (2.6 mmol) and DIEA (5.2 mmol) in NMP (10 mL) for 1 h. After DDE deprotection (3×, 2% hydrazine in DMF, RT, 3 min) and washing with DMF and NMP, fluorescein was added via pre-activated 5- and 6-carboxylfluorescein succinimidyl ester (mixed isomers, 2 mmol) (DIEA, 4 mmol; NMP, 10 mL, RT, 1 h). After washing (NMP, MeOH, DCM) the resin was dried first with air (30 min) and then under vacuum (30 min). The peptide was cleaved from the resin (with simultaneous tBu protecting group removal) under argon using TFA-TIS-water (38:1:1, 12 mL) first at 0° C. (15 min) and then at RT (75 min). The solution was filtered into a polypropylene tube and the resin was washed into the tube with cleavage cocktail and TFA. Concentration under a $N_2$ stream gave an oily residue (0.631 g) which was triturated to a solid with cold $Et_2O$. Drying under vacuum yielded 52 mg crude peptide. Reversed phase, preparative HPLC yielded 6.4 mg (4.0 μmol) 98% pure PTR 1017A (yield 0.8% from resin).

Example 2

Binding of Photo-Active Analogs to Somatostatin Receptors

The ability of the SST analogs of the invention to bind to SST receptors in vitro was demonstrated by assaying the ability of such analogs to inhibit binding of a radiolabelled SST analog to SST receptor-containing cell membranes as described above. The receptor membrane preparations used for these tests were from the cloned human receptors selectively and stably expressed in CHO cells and the radiolabelled analog used was (3-[$^{125}$I]tyrosyl$^{11}$)SRIF-14. Table 2 above describes the results of the binding assays of selected analogs to the human cloned SST-R2.

The data presented for these compounds show that the peptides of the instant invention have a high affinity of binding for SST receptors as demonstrated by the $IC_{50}$ values shown in the above table.

Example 3

Photo-Active Labeled Backbone Cyclic Peptide Analogs of PTR 3173

The compound denoted PTR 3173 having the structure GABA*-Phe-Trp-DTrp-Lys-Thr-Phe-GlyC3*-$NH_2$ is a backbone cyclized somatostatin analog selective for SST-R2 and SST-R5 with moderate affinity to hSST-R4. Its synthesis and activity are described in U.S. Pat. No. 6,355,613 and WO 99/65508. PTR 3173 was chosen as a lead for labeling due to its chemical and pharmacological properties. In addition to hSST-R subtype 2 affinity that would allow detection of most neuroendocrine-related tumors, it could provide conjugates for detection and therapy of those derived from the pituitary (expressing hSST-R5 predominantly). The core peptide is easy to synthesize and the sugar derivative, PTR-3229, retains the potency of the parent, suggesting a good site for conjugation of photo-active moieties.

Several photo-active labeled analogs based on the structure of PTR 3173 were designed, synthesized and screened for binding to hSST-R2. The synthesized compounds were based on the following formula:

Z-Lys(GABA-Phe-Trp-DTrp-Lys-Thr-Phe-GlyC3)-$NH_2$   Formula No. 2

Preferably, the photo-active moiety Z is formed by connecting the carboxy terminal of the peptide analog with a moiety selected from the group consisting of fluorescein-5-isothiocyanate wherein preferably the carbon of the isothiocyanate group is connected to the Lys alpha nitrogen through a thiourea bond; and 5- and 6-carboxylfluorescein succinimidyl ester (mixed isomers) wherein preferably the carboxy group is connected to the Lys alpha nitrogen through an amide bond.

Some of the photo-active analogs (PTR-1013A-PTR-1017A) were found to exhibit high affinity to hSST-R2 as presented in above Table 2.

Example 4

Synthesis of 96 Compounds in MPS Format

A 96-well MPS plate (YS-PDT-1) was synthesized comprising 96 photo-active labeled peptides based on four basic structures:

DPhe-Cys*-Phe-Trp-DTrp-Lys-Thr-Phe-GlyS2*-$NH_2$ (SEQ ID NO: 1) denoted PTR 3207;

GlyS2*-Phe-Trp-DTrp-Lys-Thr-Phe-GlyS2*-$NH_2$ (SEQ ID NO: 2) denoted PTR 3213;

DPhe-GlyS2*-Phe-Trp-DTrp-Lys-Thr-Phe-GlyS2*-$NH_2$ (SEQ ID NO: 3) denoted PTR 3219; and GABA*-Phe-Trp-DTrp-Lys-Thr-Phe-GlyC3*-$NH_2$ (SEQ ID NO: 4) denoted PTR 3173.

The asterisk denotes that the bridging group is connected between the $N^α$ω-functionalized derivative of the marked residue and free functional group of that residue or the second $N^α$-ω-functionalized derivative residue.

The compounds, their synthesis and activity, are described in U.S. Pat. No. 6,355,613 and WO 99/65508. Linkers/spacers were used to understand the structure-activity relationship of the distance between the often bulky (and sometimes charged, particularly when present as a metal complex), photo-active moiety and the pharmacophore.

The compounds synthesized in YS-1 plate are represented by the following generic structure: (Photo-Active Moiety)-(Linker/Spacer)-(PTR-XX) as shown in Table 3.

TABLE 3

Photo-active labeled backbone cyclized analogs of YS-PDT-1 MPS plate.

| | Fluorophore reactant | linker | PTR Core |
|---|---|---|---|
| 1 | 5-(hydroxymethyphenyl)-10,15,20-triphenyl-21,23H-porphyrin | Gly | NH-3173 |
| 2 | 5-(4-carboxyphenyl)-10,15,20-triphenyl-21,23H-porphyrin | Gly | NH-3173 |
| 3 | 5-(4-aminomethyphenyl)-10,15,20-triphenyl-21,23H-porphyrin | Gly | NH-3173 |
| 4 | 5-(4-hydroxymethyphenyl)-10,15,20-triphenyl-21,23H-chlorin # | Gly | NH-3173 |
| 5 | fluorescein-5-isothiocyanate | Gly | NH-3173 |
| 6 | Lissamine(TM) rhodamine B sulfonyl chloride # | Gly | NH-3173 |
| 7 | 5- and 6-carboxylfluorescein succinimidyl ester # | Gly | NH-3173 |
| 8 | 5-(hydroxymethyphenyl)-10,15,20-triphenyl-21,23H-porphyrin | βAla | NH-3173 |

TABLE 3-continued

Photo-active labeled backbone cyclized analogs of YS-PDT-1 MPS plate.

| | Fluorophore reactant | linker | PTR Core |
|---|---|---|---|
| 9 | 5-(4-carboxyphenyl)-10,15,20-triphenyl-21,23H-porphyrin | βAla | NH-3173 |
| 10 | 5-(4-aminomethyphenyl)-10,15,20-triphenyl-21,23H-porphyrin | βAla | NH-3173 |
| 11 | 5-(4-hydroxymethyphenyl)-10,15,20-triphenyl-21,23H-chlorin # | βAla | NH-3173 |
| 12 | 2,3,7,8,12,13,17,18-octamethyl-5-(4-hydroxymethyphenyl)-21,23H-porphyrin | βAla | NH-3173 |
| 13 | fluorescein-5-isothiocyanate | βAla | NH-3173 |
| 14 | Lissamine(TM) rhodamine B sulfonyl chloride # | βAla | NH-3173 |
| 15 | 5- and 6-carboxylfluorescein succinimidyl ester # | βAla | NH-3173 |
| 16 | 5-(hydroxymethyphenyl)-10,15,20-triphenyl-21,23H-porphyrin | GABA | NH-3173 |
| 17 | 5-(4-carboxyphenyl)-10,15,20-triphenyl-21,23H-porphyrin | GABA | NH-3173 |
| 18 | 5-(4-aminomethyphenyl)-10,15,20-triphenyl-21,23H-porphyrin | GABA | NH-3173 |
| 19 | 5-(4-hydroxymethyphenyl)-10,15,20-triphenyl-21,23H-chlorin # | GABA | NH-3173 |
| 20 | fluorescein-5-isothiocyanate | GABA | NH-3173 |
| 21 | Lissamine(TM) rhodamine B sulfonyl chloride # | GABA | NH-3173 |
| 22 | 5- and 6-carboxylfluorescein succinimidyl ester # | GABA | NH-3173 |
| 23 | 5-(hydroxymethyphenyl)-10,15,20-triphenyl-21,23H-porphyrin | aminopentanoic | NH-3173 |
| 24 | 5-(4-carboxyphenyl)-10,15,20-triphenyl-21,23H-porphyrin | aminopentanoic | NH-3173 |
| 25 | 5-(4-aminomethyphenyl)-10,15,20-triphenyl-21,23H-porphyrin | aminopentanoic | NH-3173 |
| 26 | 5-(4-hydroxymethyphenyl)-10,15,20-triphenyl-21,23H-chlorin # | aminopentanoic | NH-3173 |
| 27 | fluorescein-5-isothiocyanate | aminopentanoic | NH-3173 |
| 28 | Lissamine(TM) rhodamine B sulfonyl chloride # | aminopentanoic | NH-3173 |
| 29 | 5- and 6-carboxylfluorescein succinimidyl ester # | aminopentanoic | NH-3173 |
| 30 | 5-(hydroxymethyphenyl)-10,15,20-triphenyl-21,23H-porphyrin | aminohexanoic | NH-3173 |
| 31 | 5-(4-carboxyphenyl)-10,15,20-triphenyl-21,23H-porphyrin | aminohexanoic | NH-3173 |
| 32 | 5-(4-aminomethyphenyl)-10,15,20-triphenyl-21,23H-porphyrin | aminohexanoic | NH-3173 |
| 33 | 5-(4-hydroxymethyphenyl)-10,15,20-triphenyl-21,23H-chlorin # | aminohexanoic | NH-3173 |
| 34 | fluorescein-5-isothiocyanate | aminohexanoic | NH-3173 |
| 35 | Lissamine(TM) rhodamine B sulfonyl chloride # | aminohexanoic | NH-3173 |
| 36 | 5- and 6-carboxylfluorescein succinimidyl ester # | aminohexanoic | NH-3173 |
| 37 | 5-(hydroxymethyphenyl)-10,15,20-triphenyl-21,23H-porphyrin | Gly | 3213 |
| 38 | fluorescein-5-isothiocyanate | Gly | 3213 |
| 39 | Lissamine(TM) rhodamine B sulfonyl chloride # | Gly | 3213 |
| 40 | 5- and 6-carboxylfluorescein succinimidyl ester # | Gly | 3213 |
| 41 | 5-(hydroxymethyphenyl)-10,15,20-triphenyl-21,23H-porphyrin | βAla | 3213 |
| 42 | fluorescein-5-isothiocyanate | βAla | 3213 |
| 43 | Lissamine(TM) rhodamine B sulfonyl chloride # | βAla | 3213 |
| 44 | 5- and 6-carboxylfluorescein succinimidyl ester # | βAla | 3213 |
| 45 | 5-(hydroxymethyphenyl)-10,15,20-triphenyl-21,23H-porphyrin | GABA | 3213 |
| 46 | fluorescein-5-isothiocyanate | GABA | 3213 |
| 47 | Lissamine(TM) rhodamine B sulfonyl chloride # | GABA | 3213 |
| 48 | 5- and 6-carboxylfluorescein succinimidyl ester # | GABA | 3213 |
| 49 | 5-(hydroxymethyphenyl)-10,15,20-triphenyl-21,23H-porphyrin | aminopentanoic | 3213 |
| 50 | fluorescein-5-isothiocyanate | aminopentanoic | 3213 |
| 51 | Lissamine(TM) rhodamine B sulfonyl chloride # | aminopentanoic | 3213 |
| 52 | 5- and 6-carboxylfluorescein succinimidyl ester # | aminopentanoic | 3213 |
| 53 | 5-(hydroxymethyphenyl)-10,15,20-triphenyl-21,23H-porphyrin | aminohexanoic | 3213 |
| 54 | fluorescein-5-isothiocyanate | aminohexanoic | 3213 |
| 55 | Lissamine(TM) rhodamine B sulfonyl chloride # | aminohexanoic | 3213 |
| 56 | 5- and 6-carboxylfluorescein succinimidyl ester # | aminohexanoic | 3213 |
| 57 | 5-(hydroxymethyphenyl)-10,15,20-triphenyl-21,23H-porphyrin | Gly | 3219 |
| 58 | fluorescein-5-isothiocyanate | Gly | 3219 |
| 59 | Lissamine(TM) rhodamine B sulfonyl chloride # | Gly | 3219 |
| 60 | 5- and 6-carboxylfluorescein succinimidyl ester # | Gly | 3219 |

TABLE 3-continued

Photo-active labeled backbone cyclized analogs of YS-PDT-1 MPS plate.

| | Fluorophore reactant | linker | PTR Core |
|---|---|---|---|
| 61 | 5-(hydroxymethyphenyl)-10,15,20-triphenyl-21,23H-porphyrin | βAla | 3219 |
| 62 | fluorescein-5-isothiocyanate | βAla | 3219 |
| 63 | Lissamine(TM) rhodamine B sulfonyl chloride # | βAla | 3219 |
| 64 | 5- and 6-carboxylfluorescein succinimidyl ester # | βAla | 3219 |
| 65 | 5-(hydroxymethyphenyl)-10,15,20-triphenyl-21,23H-porphyrin | GABA | 3219 |
| 66 | fluorescein-5-isothiocyanate | GABA | 3219 |
| 67 | Lissamine(TM) rhodamine B sulfonyl chloride # | GABA | 3219 |
| 68 | 5- and 6-carboxylfluorescein succinimidyl ester # | GABA | 3219 |
| 69 | 5-(hydroxymethyphenyl)-10,15,20-triphenyl-21,23H-porphyrin | aminopentanoic | 3219 |
| 70 | fluorescein-5-isothiocyanate | aminopentanoic | 3219 |
| 71 | Lissamine(TM) rhodamine B sulfonyl chloride # | aminopentanoic | 3219 |
| 72 | 5- and 6-carboxylfluorescein succinimidyl ester # | aminopentanoic | 3219 |
| 73 | 5-(hydroxymethyphenyl)-10,15,20-triphenyl-21,23H-porphyrin | aminohexanoic | 3219 |
| 74 | fluorescein-5-isothiocyanate | aminohexanoic | 3219 |
| 75 | Lissamine(TM) rhodamine B sulfonyl chloride # | aminohexanoic | 3219 |
| 76 | 5- and 6-carboxylfluorescein succinimidyl ester # | aminohexanoic | 3219 |
| 77 | 5-(hydroxymethyphenyl)-10,15,20-triphenyl-21,23H-porphyrin | Gly | 3207 |
| 78 | fluorescein-5-isothiocyanate | Gly | 3207 |
| 79 | Lissamine(TM) rhodamine B sulfonyl chloride # | Gly | 3207 |
| 80 | 5- and 6-carboxylfluorescein succinimidyl ester # | Gly | 3207 |
| 81 | 5-(hydroxymethyphenyl)-10,15,20-triphenyl-21,23H-porphyrin | βAla | 3207 |
| 82 | fluorescein-5-isothiocyanate | βAla | 3207 |
| 83 | Lissamine(TM) rhodamine B sulfonyl chloride # | βAla | 3207 |
| 84 | 5- and 6-carboxylfluorescein succinimidyl ester # | βAla | 3207 |
| 85 | 5-(hydroxymethyphenyl)-10,15,20-triphenyl-21,23H-porphyrin | GABA | 3207 |
| 86 | fluorescein-5-isothiocyanate | GABA | 3207 |
| 87 | Lissamine(TM) rhodamine B sulfonyl chloride # | GABA | 3207 |
| 88 | 5- and 6-carboxylfluorescein succinimidyl ester # | GABA | 3207 |
| 89 | 5-(hydroxymethyphenyl)-10,15,20-triphenyl-21,23H-porphyrin | aminopentanoic | 3207 |
| 90 | fluorescein-5-isothiocyanate | aminopentanoic | 3207 |
| 91 | Lissamine(TM) rhodamine B sulfonyl chloride # | aminopentanoic | 3207 |
| 92 | 5- and 6-carboxylfluorescein succinimidyl ester # | aminopentanoic | 3207 |
| 93 | 5-(hydroxymethyphenyl)-10,15,20-triphenyl-21,23H-porphyrin | aminohexanoic | 3207 |
| 94 | fluorescein-5-isothiocyanate | aminohexanoic | 3207 |
| 95 | Lissamine(TM) rhodamine B sulfonyl chloride # | aminohexanoic | 3207 |
| 96 | 5- and 6-carboxylfluorescein succinimidyl ester # | aminohexanoic | 3207 | mixed isomers

The compounds were tested at a concentration of 10 nM, for SRIF-14 displacement on hSST-R2 expressed cells. The compounds that showed significant binding at this screening concentration, were selected for further evaluation, and accurate IC values were measured. Table 4 summarizes the analysis of the results of the most active compounds, based on the core PTR, linker and bond. All other compound tested exhibited IC50 values of above 10 nM.

FIG. 1 depicts the binding inhibition curves of the first six analogs in Table 4, which exhibit $IC_{50}$-values under 6 nM, when tested in cloned hSST-R2 expressing CHO cells.

TABLE 4

| | Analog | | | | | | | | | | | |
|---|---|---|---|---|---|---|---|---|---|---|---|---|
| | 86 | 70 | 62 | 64 | 48 | 68 | 54 | 52 | 76 | 58 | 44 | 29 |
| $IC_{50}$, nM | 1.7 | 2.9 | 3.0 | 3.9 | 5.4 | 5.7 | 48 | 9.0 | 13.0 | 18.0 | 19.0 | 32 |
| PTR | 3207 | 3219 | 3219 | 3219 | 3213 | 3219 | 3213 | 3213 | 3219 | 3219 | 3213 | 3173-NH2 |
| Linker | GABA | amino-pentanoic | βAla | βAla | GABA | GABA | (none) | amino-pentanoic | amino-hexanoic | Gly | βAla | amino-pentanoic |
| Bond* | thiourea | thiourea | thiourea | amide | amide | amide | thiourea | amide | amide | thiourea | amide | amide |
| Fluorophore | fluorescein | | | | | | | | | | | |

*Chemical bond connecting the fluorophore to the linker

Example 5

Synthesis of Additional Compounds in MPS Format

Additional photo-active labeled compounds are synthesized in 96-well MPS format. The compound's structures (YS-PDT-2 MPS plate), which are based on the sequences described in example 4, are in are depicted in Table 5.

TABLE 5

YS-PDT-2 MPS plate

| YS-2 | Fluorophore/PDT compound | Linker | PTR |
|---|---|---|---|
| 11 | 5-(4-carboxyphenyl)-10,15,20-triphenyl-21,23H-porphyrin | βAla | 3207 |
| 12 | 5-(4-hydroxymethyphenyl)-10,15,20-triphenyl-21,23H-chlorin # | βAla | 3207 |
| 14 | 5-(4-carboxyphenyl)-10,15,20-triphenyl-21,23H-porphyrin | GABA | 3207 |
| 15 | 5-(4-hydroxymethyphenyl)-10,15,20-triphenyl-21,23H-chlorin # | GABA | 3207 |
| 17 | 5-(4-carboxyphenyl)-10,15,20-triphenyl-21,23H-porphyrin | amino-pentanoic | 3207 |
| 18 | 5-(4-hydroxymethyphenyl)-10,15,20-triphenyl-21,23H-chlorin # | amino-pentanoic | 3207 |
| 20 | 5-(4-carboxyphenyl)-10,15,20-triphenyl-21,23H-porphyrin | βAla | 3219 |
| 21 | 5-(4-hydroxymethyphenyl)-10,15,20-triphenyl-21,23H-chlorin # | βAla | 3219 |
| 23 | 5-(4-carboxyphenyl)-10,15,20-triphenyl-21,23H-porphyrin | GABA | 3219 |
| 24 | 5-(4-hydroxymethyphenyl)-10,15,20-triphenyl-21,23H-chlorin # | GABA | 3219 |
| 26 | 5-(4-carboxyphenyl)-10,15,20-triphenyl-21,23H-porphyrin | amino-pentanoic | 3219 |
| 27 | 5-(4-hydroxymethyphenyl)-10,15,20-triphenyl-21,23H-chlorin # | amino-pentanoic | 3219 |
| 29 | 5-(hydroxymethyphenyl)-10,15,20-triphenyl-21,23H-porphyrin | GABA | 3213-$NH_2$ |
| 30 | 5-(hydroxymethyphenyl)-10,15,20-triphenyl-21,23H-porphyrin | aminopentanoic | 3213-$NH_2$ | mixed isomers

Example 6

In Vivo and Ex Vivo Biodistribution Monitoring of SSTR-Targeted Fluorescent Compounds The six most potent compounds of Table 4 (nos. 62, 64, 68, 70, 86 and 48), were tested in vivo and ex vivo for their biodistribution in different tissues of mice bearing subcutaneously implanted H69 human lung cancer.

Tumor Model

Balb/c nude mice xenografts inoculated subcutaneously with the human small cell lung cancer cell line, H69.

Experimental Procedures

Hundred μl of each agent (1 mM stock) were dissolved in 0.5 ml of saline and injected intravenously. For control, one mouse was injected with fluorescein.

Fluorescence measurements were performed:

1. In vivo during 24 hours after agent administrations using point (~1 $mm^2$ area) measurements by fiber-optic spectroscopic system (FOS).

2. Ex vivo 24 hours post injection using FOS.

3. Ex vivo 24 hours post injection using SD300 spectral imaging system:

Results:

Table 6 depicts the results of ex vivo fluorescence in different tissues, 24 hours after administration, measured using FOS.

TABLE 6

| | Fluorescence intensity (a.u.) Compound No. | | | | | |
|---|---|---|---|---|---|---|
| Tissue | 62 | 64 | 68 | 70 | 86 | 48 |
| Tumor | 106 ± 16 | 110 ± 17 | 97 ± 18 | 122 ± 18 | 626 ± 55 | 50 ± 20 |
| Skin | 120 ± 18 | 120 ± 18 | 77 ± 14 | 116 ± 17 | 65 ± 13 | 90 ± 20 |
| Liver | 17 ± 3 | 12 ± 2 | 35 ± 6 | 5 ± 1 | 13 ± 3 | 10 ± 5 |
| Kidney | 32 ± 5 | 20 ± 3 | 11 ± 2 | 18 ± 3 | 23 ± 5 | 15 ± 6 |
| Spleen | 4 ± 1 | 4 ± 1 | 2 ± 0.4 | 2 ± 0.3 | 7 ± 1.4 | 7 ± 2 |
| Lung | 37 ± 6 | 40 ± 6 | 35 ± 6 | 27 ± 4 | 70 ± 14 | 25 ± 8 |
| Pancreas | — | — | — | 10 ± 2 | 22 ± 6 | 16 ± 5 |

Figure 2:
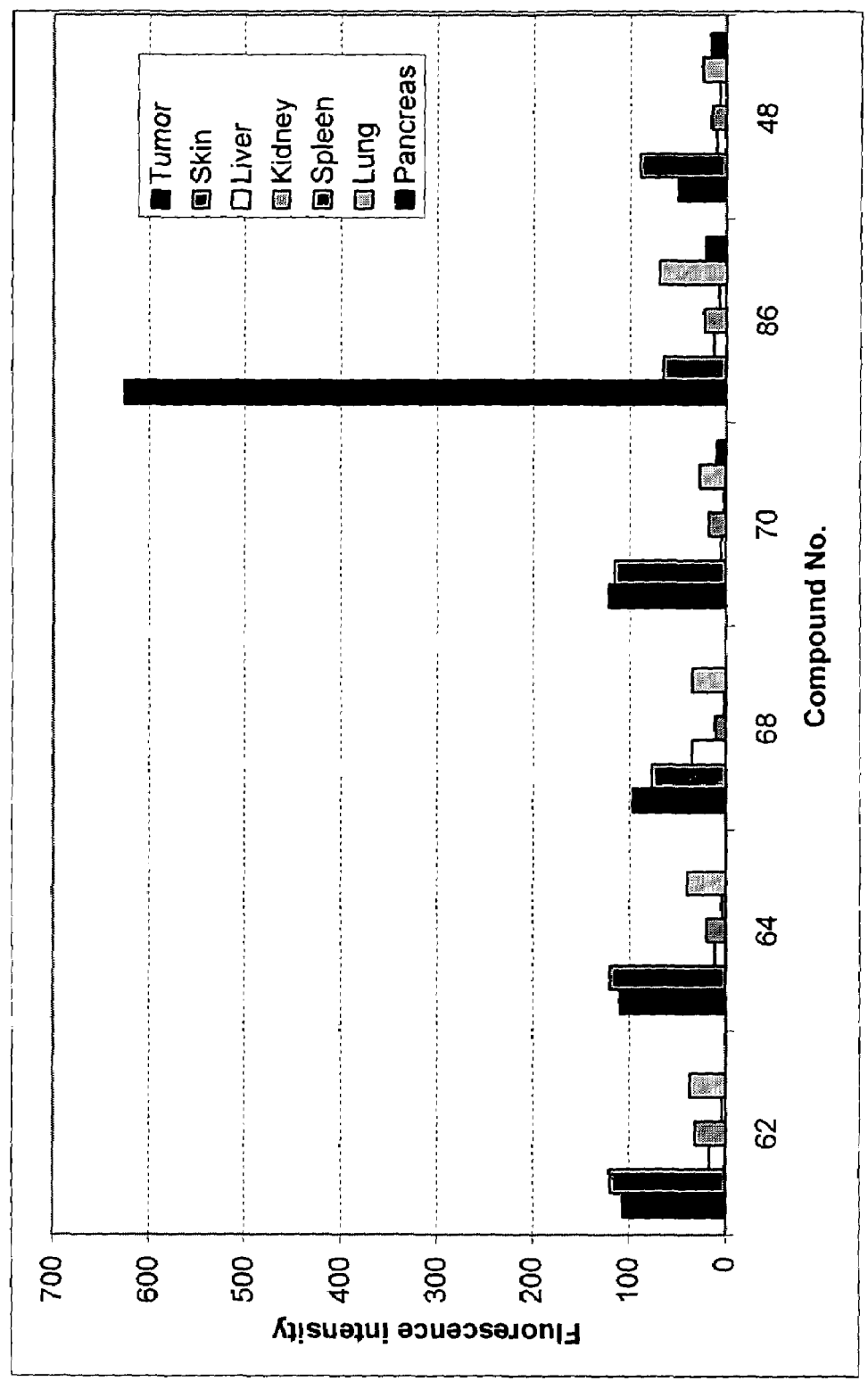
FIG. 2 depicts biodistribution in different tissues of mice bearing subcutaneously implanted H69 human lung cancer using fiber optic spectrofluorimetry.

As can be seen from Table 7 and FIG. 2, the SSTR-targeted molecules were accumulated mainly in the tumor and in the skin. Compound number 86 which has the highest affinity to SSTR-2, as shown in Table 4, also demonstrates particularly high specificity to the tumor in-vivo.

Figure 3:
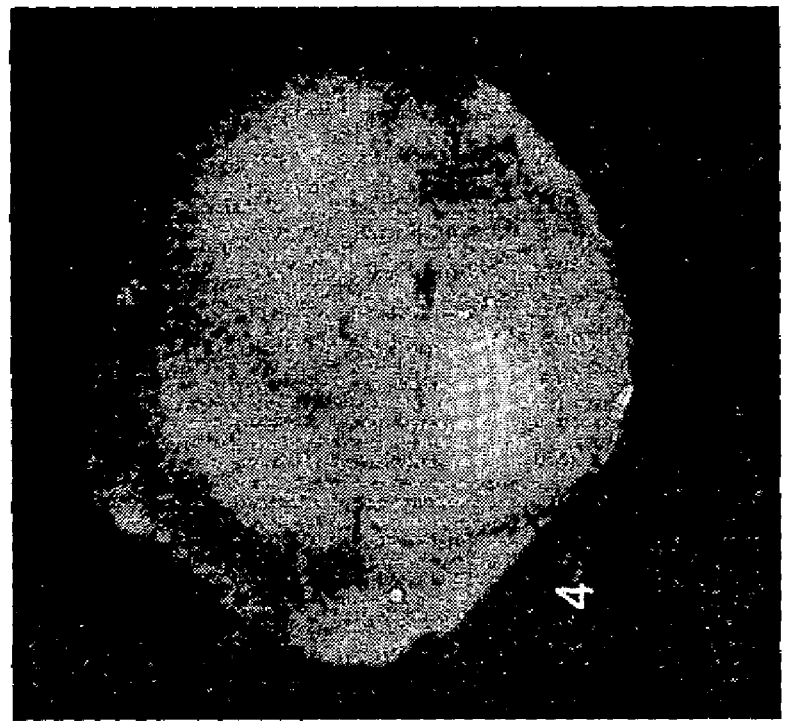
FIG. 3 shows the results of ex vivo spectral images of SSTR-targeted fluorescent compound no. 62, measured 24 h post i.v. injection to mice bearing subcutaneously implanted H69 human lung cancer. 1=lung, 2=kidney, 3=dermis, 4=tumor FIG. 4 demonstrates the results of ex vivo spectral images of SSTR-targeted fluorescent compound no. 86, measured 24 h post i.v. injection to mice bearing subcutaneously implanted H69 human lung cancer. 1=lung, 2=kidney, 3=dermis, 4=liver, 5=pancreas, 6=spleen, 7=tumor.
Figure 3:
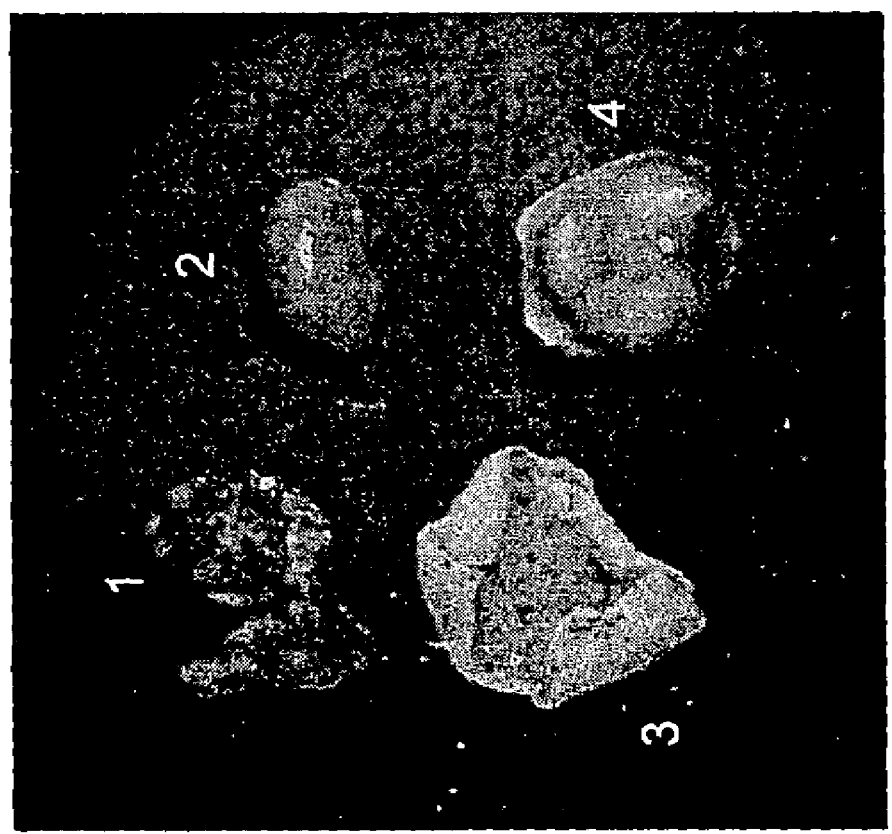
Figure 4:
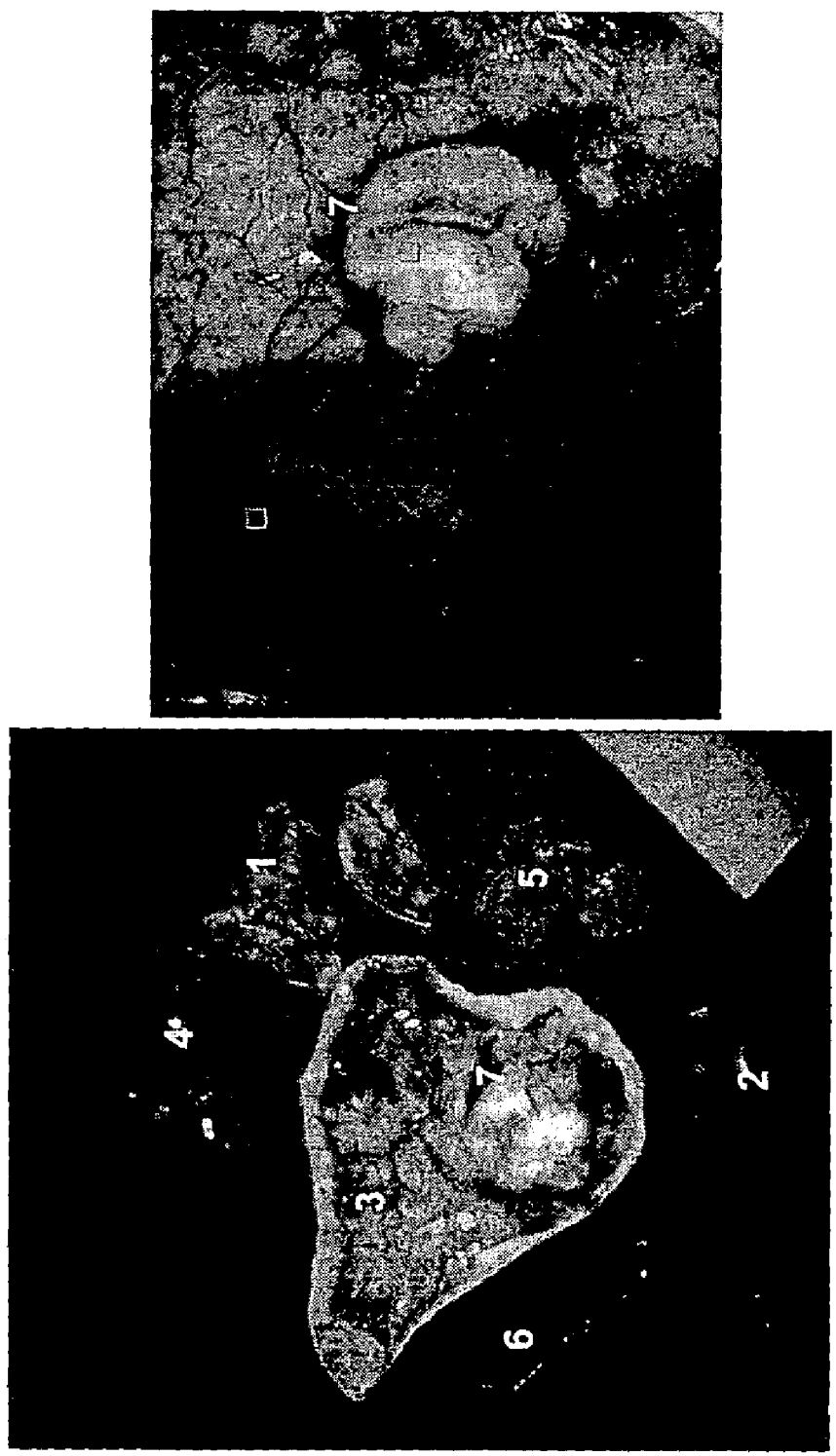

Ex vivo spectral images of SSTR-targeted fluorescent compounds measured 24 h post i.v. injection, are presented in FIGS. 3 and 4. When injecting compound no. 62 (FIG. 3) there is no (lungs and kidney) or little (dermis) fluorescence in normal organs, while the tumor exhibits high and selective fluorescence. Compound no. 86 (FIG. 4) again displays high and selective tumor fluorescence with no fluorescence in normal organs (lung, kidney, dermis, liver, pancreas, and spleen).

While the present invention has been described for certain preferred embodiments and examples it will be appreciated by the skilled artisan that many variations and modifications may be performed to optimize the activities of the peptides and analogs of the invention. The examples are to be construed as non-limitative and serve only for illustrative purposes of the principles disclosed according to the present invention, the scope of which is defined by the claims which follow.

What is claimed is:

1. A backbone cyclized analog of somatostatin having the general Formula No. 1

Z-Q-PTR            Formula No. 1 wherein Z is a photo-active moiety selected from the group consisting of 5-(4-((oxocarbonyl)methyl)phenyl)-10,15,20-triphenyl-21,23H-porphyrin; 5-(4-carboxyphenyl)-10,15,20-triphenyl-21,23H-porphyrin; 5-(4-((aminocarbonyl)methyl)phenyl)-10,15,20-triphenyl-21,23H-porphyrin; 5-(4-((oxocarbonyl)methyl)phenyl)-10,15,20-triphenyl-21,23H-chlorine (mixed isomers); 5-(aminothionyl)fluorescein; 4-sulfonyl-2-sulfo-rhodamine B; 2-sulfonyl-4-sulfo-rhodamine B (mixed isomers); and 5- and 6-carboxyfluorescein (mixed isomers); Q comprises a covalent bond selected from the group consisting of amide, carbamate, urea, thiourea, amine, and sulfonamide and PTR is selected from the group consisting of:

DPhe-Cys*-Phe-Trp-DTrp-Lys-Thr-Phe-GlyS2*-NH₂ (SEQ ID NO: 1) denoted PTR 3207;

GlyS2*-Phe-Trp-DTrp-Lys-Thr-Phe-GlyS2*-NH₂ (SEQ ID NO: 2) denoted PTR 3213;

DPhe-GlyS2*-Phe-Trp-DTrp-Lys-Thr-Phe-GlyS2*-NH₂ (SEQ ID NO: 3) denoted PTR 3219; and GABA*-Phe-Trp-DTrp-Lys-Thr-Phe-GlyC3*-NH₂ (SEQ ID NO: 4) denoted PTR 3173; and wherein the asterisks denote the cyclization points.

2. The somatostatin analog of claim 1 wherein the linker Q is connected to the N-terminal of the peptide through an amide bond.

3. The somatostatin analog of claim 1 wherein Q is selected from the group consisting of a direct bond, aminohexanoic acid, aminopentanoic acid, βAla, GABA and Gly.

4. The somatostatin analog of claim 1 comprising a backbone cyclized somatostatin analog having the general Formula No. 2

Z-Lys(GABA-Phe-Trp-DTrp-Lys-Thr-Phe-GlyC3)-NH₂            Formula No. 2 wherein Z is connected to the alpha nitrogen of the C-terminal Lysine, and the peptide within the parentheses is connected to the Lys epsilon amine and cyclized through an amide bond formed between the GABA terminal nitrogen and the Gly-C3 building unit carboxylate.

5. The somatostatin analog of claim 4 wherein the photo-active moiety Z is connected to the alpha nitrogen of the C-terminal Lysine through a bond selected from a thiourea or an amide bond.

6. The somatostatin analog of claim 1 selected from the group consisting of:

- 5- and 6-carboxyfluorescein-Dab*-Phe-Trp-DTrp-Lys-Thr-Phe-GlyC3*-NH₂;
- H-Lys(GABA*-Phe-Trp-DTrp-Lys-Thr-Phe-GlyC3*)-NH₂;
- 5- and 6-carboxyfluorescein-Lys(GABA*-Phe-Trp-DTrp-Lys-Thr-Phe-GlyC3*)-NH₂;
- 5-(aminothionyl)fluorescein-GABA-DPhe-Cys*-Phe-Trp-DTrp-Lys-Thr-Phe-GlyS2*-NH₂;
- 5-(aminothionyl)fluorescein-aminopentanoyl-DPhe-Glys2*-Phe-Trp-DTrp-Lys-Thr-Phe-GlyS2*-NH₂;
- 5-(aminothionyl)fluorescein-βAla-DPhe-GlyS2*-Phe-Trp-DTrp-Lys-Thr-Phe-GlyS2*-NH₂;
- 5- and 6-carboxyfluorescein-βAla-DPhe-GlyS2*-Phe-Trp-DTrp-Lys-Thr-Phe-GlyS2*-NH₂;
- 5- and 6-carboxyfluorescein-GABA-GlyS2*-Phe-Trp-DTrp-Lys-Thr-Phe-GlyS2*-NH₂; and
- 5- and 6-carboxyfluorescein-GABA-DPhe-Glys2*-Phe-Trp-DTrp-Lys-Thr-Phe-GlyS2*-NH₂;

and wherein the asterisks denote the cyclization points.

7. A method for optical imaging comprising administering to a patient a backbone cyclized analog of somatostatin according to claim 1.

8. The method of claim 7 wherein the photo-active moiety upon stimulation with a predetermined wavelength of light emits fluorescence.

9. The method of claim 7 wherein the photo-active moiety upon stimulation with a predetermined wavelength of light generates reactive oxygen species.

10. The method of claim 7 wherein the photo-active moiety undergoes fluorescent excitation fluorescence emission or photodynamic excitation at a wavelength greater than 630 nm.

11. The method of claim 7 wherein the somatostatin analog is administered to a patient for diagnosing cancer in the patient.

12. The method of claim 7 wherein the somatostatin analog is administered to a patient for diagnosing lung cancer in the patient.

13. The method of claim 7 wherein the somatostatin analog is administered to a patient for diagnosing small cell lung cancer in the patient.

14. A method of photodynamic therapy comprising administering to a patient in need thereof a backbone cyclized analog of somatostatin according to claim 1.

15. The method of claim 14 wherein the photo-active moiety upon stimulation with a predetermined wavelength of light emits fluorescence.

16. The method of claim 14 wherein the photo-active moiety upon stimulation with a predetermined wavelength of light generates reactive oxygen species.

17. The method of claim 14 wherein the photo-active moiety undergoes fluorescent excitation fluorescence emission or photodynamic excitation at a wavelength greater than 630 nm.

18. The method of claim 14 wherein the backbone cyclic analog is selective for one somatostatin receptor subtype.

19. The method of claim 14 wherein the backbone cyclic analog is selective for two or more somatostatin receptor subtypes.

20. The method of claim 14 wherein the somatostatin analog is administered to a patient for treating cancer in the patient.

21. The method of claim 14 wherein the somatostatin analog is administered to a patient for treating lung cancer in the patient.

22. The method of claim 14 wherein the somatostatin analog is administered to a patient for treating small cell lung carcinoma in the patient.

23. A pharmaceutical composition comprising a backbone cyclized somatostatin analog having the general Formula No. 1

Z-Q-PTR     Formula No. 1 wherein Z is a photo-active moiety selected from the group consisting of 5-(4-((oxocarbonyl)methyl)phenyl)- 10,15,20-triphenyl-21,23H-porphyrin; 5-(4-carboxyphenyl)-10,15,20-triphenyl-21,23H-porphyrin; 5-(4-((aminocarbonyl)methyl) phenyl)- 10,15,20-triphenyl-21,23H-porphyrin; 5-(4-((oxocarbonyl)methyl)phenyl)- 10,15,20-triphenyl-21,23H-chlorin (mixed isomers); 5-(aminothionyl)fluorescein; 4-sulfonyl-2-sulfo-rhodamine B; 2-sulfonyl-4-sulfo-rhodamine B (mixed isomers); and 5- and 6-carboxyfluorescein (mixed isomers ; Q comprises a covalent bond selected from the group consisting of amide, carbamate, urea, thiourea, amine, and sulfonamide; and the somatostatin analog PTR is selected from the group consisting of:

DPhe-Cys*-Phe-Trp-DTrp-Lys-Thr-Phe-GlyS2*-NH$_2$ (SEQ ID NO: 1) denoted PTR 3207;

GlyS2*-Phe-Trp-DTrp-Lys-Thr-Phe-GlyS2*-NH$_2$ (SEQ ID NO: 2) denoted PTR 3213;

DPhe-GlyS2*-Phe-Trp-DTrp-Lys-Thr-Phe-GlyS2*-NH$_2$ (SEQ ID NO: 3) denoted PTR 3219;

and GABA*-Phe-Trp-DTrp-Lys-Thr-Phe-GlyC3*-NH$_2$ (SEQ ID NO: 4) denoted PTR 3173; and wherein the asterisks denote the cyclization points.

24. The pharmaceutical composition of claim 23 wherein the linker Q is connected to the N-terminal of the peptide through an amide bond.

25. The pharmaceutical composition of claim 23 wherein Q is selected from the group consisting of a direct bond, aminohexanoic acid, aminopentanoic acid, βAla, GABA and Gly.

26. The pharmaceutical composition of claim 23 comprising a backbone cyclized somatostatin analog having the general Formula No. 2

Z-Lys(GABA-Phe-Trp-DTrp-Lys-Thr-Phe-GlyC3)-NH$_2$     Formula No. 2 wherein Z is connected to the alpha nitrogen of the C-terminal Lysine, and the peptide within the parentheses is connected to the Lys epsilon amine and cyclized through an amide bond formed between the GABA terminal nitrogen and the Gly-C3 building unit carboxylate.

27. The pharmaceutical composition of claim 26 wherein the photo-active moiety Z is a fluorescein derivative which is connected to the alpha nitrogen of the C-terminal Lysine through a bond selected from a thiourea or an amide bond.

28. The pharmaceutical composition of claim 23 wherein the backbone cyclized somatostatin analog is selected from the group consisting of:

5- and 6-carboxyfluorescein-Dab*-Phe-Trp-DTrp-Lys-Thr-Phe-GlyC3 *-NH$_2$;

H-Lys(GABA*-Phe-Trp-DTrp-Lys_Tyr-Phe-GlyC3*)-NH$_2$;

5- and 6-carboxyfluorescein-Lys(GABA*-Phe-Trp-DTrp-Lys-Thr-Phe-GlyS2*-NH$_2$;

5-(aminothionyl)fluorescein-GABA-DPhe-Cys*-Phe-Trp-DTrp-Lys-Thr-Phe-GlyS2-NH$_2$;

5-(aminothionyl)fluorescein-aminopentanoyl-DPhe-Glys2*-Phe-Trp-DTrp-Lys-Thr-Phe-GlyS2*-NH$_2$;

5-(aminothionyl)fluorescein-βAla-DPhe-GlyS2*-Phe-Trp-DTrp-Lys-Thr-Phe-Glys2*-NH$_2$;

5- and 6-carboxyfluorescein-βAla-DPhe-GlyS2*-Phe-Trp-DTrp-Lys-Thr-Phe-GlyS2*-NH$_2$;

5- and 6-carboxyfluorescein-GABA-GlyS2*-Phe-Trp-DTrp-Lys-Thr-Phe-GlyS2-NH$_2$; and 5- and 6-carboxyfluorescein-GABA-DPhe-Glys2*-Phe-Trp-DTrp-Lys-Thr-Phe-GlyS2*-NH$_2$;

and wherein the asterisks denote the cyclization points.

29. The pharmaceutical composition of claim 23 wherein the backbone cyclic analog is selective for one somatostatin receptor subtype.

30. The pharmaceutical composition of claim 23 wherein the backbone cyclic analog is selective for two or more somatostatin receptor subtypes.

* * * * *

UNITED STATES PATENT AND TRADEMARK OFFICE
CERTIFICATE OF CORRECTION

PATENT NO. : 7,700,717 B2
APPLICATION NO. : 10/950378
DATED : April 20, 2010
INVENTOR(S) : Bonasera et al.

It is certified that error appears in the above-identified patent and that said Letters Patent is hereby corrected as shown below:

Title Page:
Item (75) Inventors, please change the city and country of residence of Thomas A. Bonasera from "Milan (IL)" to -- Cambridge (UK) --.
Item (56) References Cited, FOREIGN PATENT DOCUMENTS:
  "JP   200342297" to -- JP   2000342297 --.
  Add the following foreign patent document: -- DE   19917713   10/2000 --.
Item (56) References Cited, OTHER PUBLICATIONS:
  Marco Del Governatore et al. reference, change "4200-4255" to -- 4200-4205 --.
  David G. Hilmey et al. reference, change "vol. 7" to -- vol. 45 --.

Column 39:
Line 43 (claim 1, line 10), change "chlorine" to -- chlorin --.

Column 41:
Line 64 (claim 23, line 14), change "(mixed isomers;" to -- (mixed isomers); --.

Column 42:
Line 39 (claim 28, line 6), after "H-Lys(GABA*-Phe-Trp-DTrp-Lys", change "_Tyr" to -- -Thr --.
Line 42 (claim 28, line 9), after "Lys-Thr-Phe-", change "GlyS2*" to -- GlyC3*) --.
Line 44 (claim 28, line 11), after "Trp-DTrp-Lys-Thr-Phe-", change "GlyS2" to -- GlyS2* --.
Line 52 (claim 28, line 19), after "DTrp-Lys-Thr-Phe-", change "GlyS2" to -- GlyS2* --.

Signed and Sealed this

Twenty-fifth Day of May, 2010

David J. Kappos
*Director of the United States Patent and Trademark Office*

```
                         SEQUENCE LISTING

<160> NUMBER OF SEQ ID NOS: 5

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: N acylated amino acid
<222> LOCATION: (9)..(9)
<223> OTHER INFORMATION:
<220> FEATURE:
<221> NAME/KEY: MOD_RES
<222> LOCATION: (9)..(9)
<223> OTHER INFORMATION: AMIDATION
<220> FEATURE:
<221> NAME/KEY: MOD_RES
<222> LOCATION: (1)..(1)
<223> OTHER INFORMATION: D isomer
<220> FEATURE:
<221> NAME/KEY: MOD_RES
<222> LOCATION: (5)..(5)
<223> OTHER INFORMATION: D isomer
<220> FEATURE:
<221> NAME/KEY: MISC_FEATURE
<222> LOCATION: (2)..(9)
<223> OTHER INFORMATION: backbone-side chain cyclization between
      residues 2 and 9

<400> SEQUENCE: 1

Phe Cys Phe Trp Trp Lys Thr Phe Gly
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: backbone-backbone cyclization between residues
      1 and 8
<220> FEATURE:
<221> NAME/KEY: MOD_RES
<222> LOCATION: (1)..(1)
<223> OTHER INFORMATION: ACETYLATION - N acylated amino acid
<220> FEATURE:
<221> NAME/KEY: MOD_RES
<222> LOCATION: (8)..(8)
<223> OTHER INFORMATION: ACETYLATION - N acylated amino acid
<220> FEATURE:
<221> NAME/KEY: MOD_RES
<222> LOCATION: (8)..(8)
<223> OTHER INFORMATION: AMIDATION
```

```
<400> SEQUENCE: 2

Gly Phe Trp Trp Lys Thr Phe Gly
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D isomer
<220> FEATURE:
<221> NAME/KEY: MISC_FEATURE
<222> LOCATION: (2)..(9)
<223> OTHER INFORMATION: backbone-backbone cyclization between residues
      2 and 9
<220> FEATURE:
<221> NAME/KEY: MOD_RES
<222> LOCATION: (5)..(5)
<223> OTHER INFORMATION: D isomer
<220> FEATURE:
<221> NAME/KEY: MOD_RES
<222> LOCATION: (2)..(2)
<223> OTHER INFORMATION: ACETYLATION - N acylated amino acid
<220> FEATURE:
<221> NAME/KEY: MOD_RES
<222> LOCATION: (8)..(8)
<223> OTHER INFORMATION: ACETYLATION - N acylated amino acid
<220> FEATURE:
<221> NAME/KEY: MOD_RES
<222> LOCATION: (8)..(8)
<223> OTHER INFORMATION: AMIDATION

<400> SEQUENCE: 3

Phe Gly Phe Trp Trp Lys Thr Phe Gly
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is selected from aminohexanoic acid,
      aminopentanoic acid, GABA, beta-Ala and Gly
<220> FEATURE:
<221> NAME/KEY: MISC_FEATURE
<222> LOCATION: (1)..(8)
<223> OTHER INFORMATION: N-terminal-backbone cyclization between
      residues 1 and 8
<220> FEATURE:
<221> NAME/KEY: MOD_RES
<222> LOCATION: (4)..(4)
<223> OTHER INFORMATION: D isomer
<220> FEATURE:
<221> NAME/KEY: MOD_RES
<222> LOCATION: (8)..(8)
<223> OTHER INFORMATION: ACETYLATION - N acylated amino acid
<220> FEATURE:
<221> NAME/KEY: MOD_RES
<222> LOCATION: (8)..(8)
<223> OTHER INFORMATION: AMIDATION

<400> SEQUENCE: 4

Xaa Phe Trp Trp Lys Thr Phe Gly
1               5
```

```
<210> SEQ ID NO 5
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: X = GABA
<220> FEATURE:
<221> NAME/KEY: MISC_FEATURE
<222> LOCATION: (2)..(9)
<223> OTHER INFORMATION: N-terminal-backbone cyclization between
      residues 2 and 9
<220> FEATURE:
<221> NAME/KEY: MOD_RES
<222> LOCATION: (5)..(5)
<223> OTHER INFORMATION: D Isomer
<220> FEATURE:
<221> NAME/KEY: MOD_RES
<222> LOCATION: (9)..(9)
<223> OTHER INFORMATION: AMIDATION
<220> FEATURE:
<221> NAME/KEY: MOD_RES
<222> LOCATION: (9)..(9)
<223> OTHER INFORMATION: ACETYLATION - N acylated amino acid

<400> SEQUENCE: 5

Lys Xaa Phe Trp Trp Lys Thr Phe Gly
1               5
```